United States Patent
Voskuhl

(10) Patent No.: US 8,658,627 B2
(45) Date of Patent: *Feb. 25, 2014

(54) PREGNANCY HORMONE COMBINATION FOR TREATMENT OF AUTOIMMUNE DISEASES

(75) Inventor: Rhonda Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 916 days.

This patent is subject to a terminal disclaimer.

(21) Appl. No.: 12/451,892

(22) PCT Filed: Jun. 4, 2008

(86) PCT No.: PCT/US2008/007065
§ 371 (c)(1),
(2), (4) Date: Mar. 17, 2010

(87) PCT Pub. No.: WO2008/150547
PCT Pub. Date: Dec. 11, 2008

(65) Prior Publication Data
US 2010/0203016 A1    Aug. 12, 2010

Related U.S. Application Data

(63) Continuation-in-part of application No. 11/151,040, filed on Jun. 13, 2005, which is a continuation of application No. 10/131,834, filed on Apr. 24, 2002, now Pat. No. 6,936,599.

(60) Provisional application No. 60/286,842, filed on Apr. 25, 2001, provisional application No. 60/933,030, filed on Jun. 4, 2007.

(51) Int. Cl.
*A61K 31/56* (2006.01)

(52) U.S. Cl.
USPC .................................................. 514/170

(58) Field of Classification Search
USPC ................................................ 514/171, 170
See application file for complete search history.

(56) References Cited

U.S. PATENT DOCUMENTS

| 5,200,197 A | 4/1993 | Wright et al. |
| 5,554,601 A | 9/1996 | Simpkins et al. |

(Continued)

FOREIGN PATENT DOCUMENTS

| WO | WO 97/08188 | 3/1997 |
| WO | WO 99/48502 | 9/1999 |

(Continued)

OTHER PUBLICATIONS

Trooster et al., International Journal of Immunopathology, 1994;7(3):183-192.*

(Continued)

*Primary Examiner* — San-Ming Hui
(74) *Attorney, Agent, or Firm* — McDermott Will & Emery LLP

(57) ABSTRACT

The present invention relates to pregnancy hormone combinations and methods of treatment for autoimmune diseases having at least two hormonal components, a pregnancy hormone (such as estriol), and a gestagen (such as levonorgestrel or norethindrone) thereby providing for the continuous, uninterrupted administration of pregnancy hormones for the treatment for autoimmune disorders, such as multiple sclerosis.

18 Claims, 5 Drawing Sheets

(56) References Cited

U.S. PATENT DOCUMENTS

| | | | |
|---|---|---|---|
| 6,013,642 | A | 1/2000 | Foulkes et al. |
| 6,043,236 | A | 3/2000 | Brattsand et al. |
| 6,214,791 | B1 | 4/2001 | Arnon et al. |
| 2001/0016325 | A1 | 8/2001 | Mobley et al. |
| 2002/0164314 | A1 | 11/2002 | Weiss et al. |
| 2002/0183299 | A1* | 12/2002 | Voskuhl .................. 514/182 |
| 2004/0229800 | A1 | 11/2004 | Gold |
| 2005/0239758 | A1* | 10/2005 | Roby ..................... 514/170 |
| 2005/0239762 | A1 | 10/2005 | Voskuhl |

FOREIGN PATENT DOCUMENTS

| | | |
|---|---|---|
| WO | WO 01/85154 | 11/2001 |
| WO | WO 03/072109 | 9/2003 |
| WO | WO 03/072110 | 9/2003 |
| WO | WO 2006/053172 | 5/2006 |
| WO | WO 2007038435 | 4/2007 |
| WO | WO 2007038636 | 4/2007 |

OTHER PUBLICATIONS

Jansson et al., Journal of Neuroimmunology, 1994;53:203-207.*

Offner H.; Adlark K.; Zamora A.; Vandenbark A.A. "Estrogen potentiates treatment with T-cell receptor protein of female mice with experimental encephalomyelitis." Journal of Clinical Investigation, May 2000, 105(10):1465-72.

Offner, Halina; Adlard, Kirsten; Zamora, Alex; Vandenbark, Arthur A. Estrogen potentiates treatment with TCR protein of female mice with experimental encephalomyelitis. (Joint Meeting of the 5th World Congress on Advances in Oncology and the 3rd International Symposium on Molecular Medicine Crete, Greece Oct. 19-21, 2000) International Journal of Molecular Medicine. 2000. 6(Supplement 1):58.

Polman, C.H. and Hartung, H.P., "The Treatment of Multiple Sclerosis: Current and 25 Future", Current Opinion in Neurology, 8(3):200-9, Jun. 1995.

Powell, M.D., Mitchell, D., Lederman, J., Buckmeier, J., Zamvil, S.S., Graham, M., Ruddle, N.H., Steinman, L., "Lymphotoxin and Tumor Necrosis Factor-Alpha Production by Myelin Basic Protein Specific T Cell Clones Correlates with Encephalitogenicity," Int. Immunol., 2:539-544, 1990.

Pratt, et al., "Estriol Production Rates and Breast Cancer," Journal of Clinical Endocrinology & Metabolism, 46:44-47,1978.

Rep, van Oosten, Roos, Ader, Polman, van Lier, "Treatment with Depleting CD4 Monoclonal Antibody Results in a preferential Loss of Circulating Naive T Cells But Does Not Affect IFN-Gamma Secreting TH I Cells in Humans," J. of Clin. Investig., 99(9):2225-2231, May 1, 1997.

Rott, O., Fleisher, B. and Cash, E., "Interleukin-IO Prevents Experimental Allergic Encephalomyelitis in Rats," Eur. J. Irnmunol, 24: 1434-1440, 1994.

Rudick, R.A., Ransohoff, R.M., Lee, J.e. et al. "In vivo effects of interferon beta-I a on immunosuppressive cytokines in multiple sclerosis," [published erratum appears in Neurology Jul. 1998; 51(1):332]. Neurology 1998; 50:1294-300.

Runmarker, B. and Anderson, O., (1995) "Pregnancy is Associated with a Lower Risk of Onset and a Better Prognosis in Multiple Sclerosis." Brain 118, 253-6.

Ryan, K. D., and N.B. Schwartz. 1980. "Changes in serum hormone levels associated with male-induced ovulation in group-housed adult female mice." Endocrinology 106:959.

Sadovnick, A.D., "Update on Management and Genetics of Multiple Sclerosis", Jour. of 10 Neural Transmission, Supplementum, 50:167-72,1997.

Sanchez-Guerrero, J., Liang, M.H., Karlson, E. W., Humnter, OJ., Colditz, G.A., "Postmenopausal Estrogen Therapy and the Risk for Developing Systemic Lupus Erythematosus," Ann. Int. Med., 122:430-433, 1995.

Sandor, S. & Leahy, R. "Surface-based labeling of cortical anatomy using a deformable atlas." IEEE Transactions on Medical Imaging 1997; 16:41-54.

Sandyk, R. "Estrogen's impact on cognitive functions in multiple sclerosis." International Journal of Neuroscience 1996; 86:23-31.

Schmidt, J.B., Binder, M., Desschik, G., Bieglmayer, E. and Reiner, A., "Treatment of Skin Aging with Topical Estrogens", International Journal of Dermatology, 35(9):669-74, Sep. 1996.

Schmidt, J.B. Binder, M. Macheiner, W., Bieglmayer, E., "New Treatment of Atrophic 20 Acne Scars by Iontophoresis with Estriol and Tretinoin", International Journal of Dermatology, 34(1):53-7, Jan. 1995.

Schountz, T., Kasselman, J.P., Martinson, F.A., Brown, L. and Murray, J.S., "MHC Genotype Controls the Capacity of Ligand Density to Switch T Helper (Th)-Irrh-2 Priming in Vivo," J. Immunol., 157:3893-3901, 1996.

Sicotte, Nancy; Pfieffer, Paul; Klutch, Rochelle; Odesa, Sylvia; Bouvier, Seth; Wu, Jackson; Alger, Jeffrey; Voskuhl, Rhonda R. "Treatment of women with multiple sclerosis using the pregnancy hormone estriol: A Pilot Study." (53rd Annual Meeting of the American Academy of Neurology Philadelphia, PA, USA May 5-11, 2001) Neurology. Apr. 24, 2001 . 56(8 Supplement 3):A 75.

Smith, R. and Studd, JW.W.W., "A Pilot Study of the Effect Upon Multiple Sclerosis of the Menopause, Hormone Replacement Therapy and the Menstrual Cycle," J. Royal Soc. Med, 85:612-613, 1992.

Stinissen, P., Raus, J., and Zhang, J., "Autoimmune Pathogenesis of Multiple Sclerosis: Role of Autoreactive T Lymphocytes and New Immunotherapeutic Strategies" Critical Reviews in Immunology, 17(1):33-75, 1997.

Suenaga, R., Evans, M.1., Mitamura, K. et al. "Peripheral blood T cells and monocytes and B cell lines derived from patients with lupus express estrogen receptor transcripts similar to those of normal cells." J Rheumatol 1998; 25: 1305-12.

Thompson, A. J., "Multiple Sclerosis: Symptomatic Treatment", J Neurology, 243(8):559-565, 1996.

Thorogood, M.; Hannaford P.C. "The influence of oral contraceptives on the risk of multiple sclerosis." British Journal of Obstetrics and Gynaecology, Dec. 1998, I 05( 12): 1296-9.

Trapp, B.D., Bo, L., Mork, S. & Chang, A. "Pathogenesis of tissue injury in MS lesions." Journal of Neuroimmunology 1999; 98:49-56.

Trapp, B.D., Ransohoff, R. & Rudick, R. "Axonal pathology in multiple sclerosis: relationship to neurologic disability." Current Opinion in Neurology 1999; 12:295-302.

Tzingounis, V.A., Feridun-Aksu, M. And Greenblatt, R.B. "Estriol in the Management of the Menopause," JAMA, 239: 1638-1641, 1978.

Utian, W. "The Place of Oestriol Therapy After Menopause," Acta Endocrinologic Suppl., 233 :51-56,1980.

Vakil, D., Morgan, R. W. and Elinson, L., "Benign Breast Disease: Estriol Proportions and Family History of Breast Cancer," Cancer Detection and Prevention, 4:517-523, 1981.

Van Boxel-Dezaire, A.H., Holt, S.C., van Oosten, B.W. et al. "Decreased interleukin-IO and increased interleukin-12p40 mRNA are associated with disease activity and characterize different disease stages in multiple sclerosis." Ann Neurol 1999; 45:695-703.

Vandenbark, A.A., Morgan, E., Bartholomew, R. et al. "TCR peptide therapy in human autoimmune diseases." Neurochem Res 2001; 26:713-30.

Vandenbark, Chou, Whitham, Mass, Buenafe, Liefeld, Kavanagh, Cooper, Hashim, OITner, et al., "Treatment of Multiple Sclerosis With T-Cell Receptor Peptides: Results of a Double-Blind Pilot Trial," Nature Medicine, 2 (10):1109-1115, Oct. 1996.

Verghese, J., Kuslansky, G., Katz, MJ. et al. "Cognitive performance in surgically menopausal women on estrogen." Neurology 2000; 55:872-4.

Villard-Mackintosh, L., and Vessey, M.P., "Oral Contraceptives and Reproductive Factors in Multiple Sclerosis Incidence," Contraception, 47: 161-168, 1993.

Volpe, A., Facchinette, F., Grasso, A., Petraglia, F., Carnpanini, D. and Gennazzani, A.R., "Benefits and Risks of Different Hormonal Replacement Therapies in Post-Menopausal Women," Maturitas, 8:327-334,1986.

(56) References Cited

OTHER PUBLICATIONS

Voskuhl, R.R. and Palaszynski, K.M. (2001) "Female Sex Hormones at Supraphysicologic, but not Physiologic, Levels Decrease EAE Severity in Female SJL mice." FASEB Journal IS, A372.

Voskuhl, R.R. & Palaszynski, K. "Sex hormones in experimental autoimmune encephalomyelitis: Implications for multiple sclerosis." The Neuroscientist 2001; 7:258-270.

Voskuhl, R.R., Martin, R. & McFarland, H.F. "A functional basis for the association of HLA class II genes and susceptibility to multiple sclerosis: cellular immune responses to myelin basic protein in a multiplex family." Journal of Neuroimmunology 1993; 42: 199-207.

Watkins-Smith, O., et al., "Quantitative Estimation of Estrogen Conjugates in Late 20 Pregnancy Plasma," J. Clin. Endocrionol, 25 :732-741, 1965.

Wegmann, T.G., Lin, H., Guilbert, L., Mosrnann, T.R., "Bidirectional Cytokine Interactions in the Maternal-Fetal Relationship: Is Successful Pregnancy a Th2 Phenomenon?" Immunol. Today, 14:353-356, 1993.

Zorgdrager, A. and De Keyser, J. (1997), "Menstrually Related Worsening of Symptoms in Multiple Sclerosis." Journal of the Neurological Sciences 149, 95-7.

[No author] "Risks and benefits of estrogen plus progestin in healthy postmenopausal women: Principal results from the Women's Health Initiative randomized controlled trial." JAMA 2002, vol. 288: pp. 321-333.

Behl, C. et al. "17-Beta estradiol protects neurons from oxidative stress-induced cell death in vitro." Biochem Biophys Res. Commun. 1995, vol. 216: pp. 473-482.

Behl, C. et al. "Neuroprotection against oxidative stress by estrogens: Structure-activity relationship." Mol. Pharmacol. 1997, vol. 51: pp. 535-541.

Cutolo, M. "Sex hormone adjuvant therapy in rheumatoid arthritis." Rheum. Dis. Clin North Am 2000, vol. 26: pp. 881-895.

Drake, E.B. et al. "Associations between circulating sex steroid hormones and cognition in normal elderly women." Neurology 2000, vol. 54: pp. 599-603.

Drossaers-Bakker, KW. et al. "Pregnancy and oral contraceptive use do not significantly influence outcome in long term rheumatoid arthritis." Ann. Rheum. Dis 2002, vol. 61: pp. 405-408.

Du, C. et al. "Administration of dehydroepiandrosterone suppresses experimental allergic encephalomyelitis in EJL/J mice." Journal of Immunology, 2001, pp. 7094-7101.

Head, K.A. "Estriol: Safety and efficacy." Alternative Med. Rev. 1998, vol. 3: pp. 101-113.

Jansson, L. et al. "Estrogen-mediated immunosuppression in autoimmune diseases." Inflammation research 1998, vol. 47: pp. 290-301.

Jover, T. et al. "Estrogen protects against global ischemia-induced neuronal death and prevents activation of apoptotic signaling cascades in the hippocampal CA 1." J. Neurosci. 2002, vol. 22: pp. 2115-2124.

Galea et al., "Estradiol alleviates depressive-like symptoms in a novel animal model of post-partum depression." Behavioural Brain Research, vol. 122, No. 1, pp. 1-9 (2001).

Jansson et al., "Estrogen induces a potent suppression of experimental autoimmune encephalomyelities and collagen-induced arthritis in mice", Journal of Neuroimmunology, vol. 53, No. 2, pp. 203-207 (1994).

Kim et al., "Estriol ameliorates autoimmune demyelinating disease", Neurology, vol. 52, No. 6, pp. 1230-1236 (1999).

Hall et al., "Beta-interferon and multiple sclerosis", Trends of Neuroscience, vol. 20, pp. 63-67 (1997).

Search Report in European Patent Application No. 06815626.4 dated Nov. 18, 2010.

Office Action in Canadian Patent Application No. 2,623,839 dated Nov. 17, 2011.

Office Action in European Patent Application No. 02729034.5 dated Oct. 11, 2007.

Search Report in European Patent Application No. 02729034.5 dated Dec. 22, 2004.

Search Report in European Patent Application No. 06815340.2 dated Nov. 10, 2010.

International Preliminary Report on Patentability in PCT/US2006/037259 dated Apr. 3, 2008.

International Search Report issued by the International Search Authority for PCT/US2002/013407 mailed Aug. 22, 2002.

Written Opinion issued by the International Search Authority for PCT/US2002/013407 mailed Jan. 16, 2003.

International Preliminary Report on Patentability and Written Opinion in PCT/US2006/037752 mailed Apr. 3, 2008.

International Search Report and Written Opinion for PCT/US2006/037752 dated Sep. 25, 2007.

International Preliminary Examination Report in PCT/US2002/013407, dated Nov. 14, 2003.

International Search Report and Written Opinion for PCT/US2006/037259 dated Mar. 28, 2007.

Supplementary Search Report in European Patent Application No. 08754819.4 dated Aug. 10, 2010.

International Search Report and Written Opinion for PCT/US2008/012353 dated Feb. 6, 2009.

International Preliminary Report on Patentability for PCT/US2008/012353 dated May 3, 2011.

Hauptmann et al. "Concepts for the syntheses of biotinylated steroids. Part II: 17beta-estradiol derivatives as immunochemical probes." Bioconjug Chem., 2000, 11, 537-48.

Sylvia et al. "17 beta-estradiol-BSA conjugates and 17 beta-estradiol regulate growth plate chondrocytes by common membrane associated mechanisms involving PKC dependent and independent signal transduction." J Cell Biochem., 2001, 81, 413-29.

Abramsky, O. Pregnancy and multiple sclerosis. Annals of Neurology 1994; 36 Suppl:S38-41.

Aharoni, R., Teitelbaum, D., Sela, M. & Amon, R. Bystander suppression of experimental autoimmune encephalomyelitis by T cell lines and clones of the Th2 type induced by copolymer I. Journal of Neuroimmunology 1998; 91: 135-46.

Ando, D., Clayton, J., Kono, D., Urban, J., Sercarz, E.E., "Encephalitogenic T Cells in the BIO.PL Model of Experimental Allergic Encephalomyelitis (EAE) Are of the Th1 Lymphokine Subtype," Cell. Immunol., 124: 132-143, 1989.

Asthana, S., Baker, L.D., Craft, S. et al. "High-Dose Estradiol Improves Cognition for Women with AD: Results of a Randomized Study," Neurology, 2001; 57:605-12.

Balashov, K.E., Comabella, M., Ohashi, T. et al. Defective regulation of IFNgamma and IL-12 by endogenous IL-IO in progressive MS. Neurology 2000; 55: 192-8.

Barkhof, F., van Waesberghe, J.H., Filippi, M. et al. T(1) hypo intense lesions in secondary progressive multiple sclerosis: effect of interferon beta-I b treatment. Brain 200 I; 124: 1396-402.

Barkley, M. S., B. L. Lesley, M. A. Thompson, and C. H. Shackleton. 1985. Equol: a contributor to enigmatic immunoassay measurements of estrogen. Steroids 46:587.

Becker, C.C., Gidal, B.E. and Fleming, J.O., "Immunotherapy in Multiple Sclerosis", Amer. Journal of Health System Pharmacy, 52(19):2105-20, Oct. 1, 1995.

Bijisma, J.W. and Van der Brink, H.R., "Estrogens and Rheumatoid Arthritis," American Journal of Reproductive Immunology, 28:231-234, 1992.

Birk, K. et al., (1990) The Clinical Course of Multiple Sclerosis During Pregnancy and the Puerperium, Arch Neurol, 47,738-42.

Birk, K., Smeltzer, S.c. and Rudick, R. (1998) Pregnancy and Multiple Sclerosis, Semin Neurol 8, 205-13.

Bongioanni, Durelli, Ferrero, Imperiale, Oggero, Verdun, Aimo, Pagni, Geuna, Bergamasco. "Systemic High-Dose Recombinant-alpha-2a-Interferon Therapy Modulates Lymphokine Production in Multiple Sclerosis." J. Neurolog. Sci., 143 (1-2):91-99, Nov. 1996.

Boothman, B.R., "Interferon Beta: The Current Position", British Jour. of Hospital Medicine, 57(6):277-80, Mar. 19-Apr. 1, 1997.

Boumpas, D.T., Fessler, B.J., Austin, H.A., Balow, J.E., Klippel, J.H., Lockshin, M.D. "Systemic Lupus Erythematosus: Emerging Concepts." Annals of Internal Medicine, 123:42-53, 1995.

Brod, S.A. Lindsey, J.W. and Wolinsky, J.S. "Multiple Sclerosis: Clinical Presentation, Diagnosis and Treatment." Amer. Family Physician, 54(4):1301-6,1309-11, Sep. 15, 1996.

(56) References Cited

OTHER PUBLICATIONS

Brod, S.A., Marshall, Henninger, Sriram, Khan, Wolinsky, J.S., "Interferon-beta Ib Treatment Decreases Tumor Necrosis Factor-beta and Increases Interleukin-6 Production in Multiple Sclerosis," Neurology, 46(6): 1633-1638, Jun. 1996.

Brostoff and Gold, "Results of a Phase I Clinical Trial of a T-Cell Receptor Peptide Vaccine in Patients with Multiple Sclerosis. J. Analysis of T-Cell Receptor Utilization in CSF Cell Populations," Journal of Neuroimmunology 76(1-2): 15-28, Jun. 1997.

Cannella, B., Gao, Y.L., Brosnan, C. Raine, C.S., "IL-10 Fails to Abrogate Experimental Autoimmune Encephalomyelitis," Journal of Neuroscience Research, 45:735-746, 1996.

Cardozo, L., Rekers, H., Tapp, A., Barnick, C., Shepherd, A., Schussler, B., Kerr-Wilson, R., Van Geelan, J., Barlebo, H., and Walter, S., "Oestriol in the Treatment of Postrnenopausal Urgency: A Multicentre Study," Maturitas, 18 (1):47-53, Dec. 1993.

Cheng, G., Liu, I., Zhang, Q., Fan, W., Ye, H., Wang, Z. and Pan, H., "Nylestriol Replacement Therapy in Postmenopausal Women," Chinese Medical Journal, 106:911-916, 1993.

Comi, G., Filippi, M. & Wolinsky, J.S. "European/Canadian multicenter, double-blind, randomized, placebo-controlled study of the effects of glatiramer acetate on magnetic resonance imaging-measured disease activity and burden in patients with relapsing multiple sclerosis." European/Canadian Glatiramer Acetate Study Group. Ann Neuro 2001; 49:290-7.

Confavreux, C., Hutchinson, M., Hours, M.M. et al. "Rate of pregnancy-related relapse in multiple sclerosis." Pregnancy in Multiple Sclerosis Group. New England Journal of Medicine 1998; 339:285-91.

Correale, J., Arias, M. & Gilmore, W. "Steroid hormone regulation of cytokine secretion by proteolipid protein-specific CD4+ T cell clones isolated from multiple sclerosis patients and normal control subjects." Journal of Immunology 1998; 161:3365-74.

Crisi, G.M., Santambrogio, L., Hochwald, G.M., Smith, S.R., Carlino, I.A. and Thorbecke, G.J., "Staphylococcal Enterotoxin Band Tumor-Necrosis Factor-alpha-Induced Relapses of Experimental Allergic Encephalomyelitis: Protection by Transforming Growth Factor-Beta and Interleukin-IO," European Journal of Immunology, 25:3035-3040, 1995.

Da Silva, J.A. and Hall, G.M., "The Effects of Gender and Sex Hormones on Outcome in Rheumatoid Arthritis," Baillieres Clinical Rheumatology, 6:196-219,1992.

Da Silva, J.A. and Spector, T.D., "The Role of Pregnancy in the Course and Aetiology of Rheumatoid Arthritis, Clinical Rheumatology," pp. 189-194, 1992.

Damek, D.M. & Shuster, E.A. "Pregnancy and multiple sclerosis." Mayo Clinic Proceedings 1997; 72:977-89.

DeGroot, L.J. And Jameson, J.L., 1994. Endocrinology, vol. 3, Part 9, pp. 2171-2223.

Delassus, S., Coutinho, G.C., Saucier, C., Darche, S., Kourlisky, P., "Differential Cytokine Expression in Maternal Blood and Placenta During Murine Gestation," J. Immunol., 152:2411-2420, 1994.

Office Action in European Patent Application No. 02729034.5 dated Jul. 22, 2005.

Drew, P.D. & Chavis, J.A. "Female sex steroids: effects upon microglial cell activation." J Neuroimmunol 2000; 111:77-85.

Duda, P.W., Schmied, M.C., Cook, S.L. et al. "Glatiramer acetate (Copaxone) induces degenerate, Th2-polarized immune responses in patients with multiple sclerosis." Journal of Clinical Investigation 2000; 105:967-76.

Follingstad, A.H., et al., "Estriol, the Forgotten Estrogen?" JAMA, 239:29-30, 1978.

Fritzmeier, K.H., et al. (2001) Analysis of the Effects ofERbeta on ERalpha Transcriptional Activity Using Isotope Selective Ligands. Experimental and Clinical Endocrinology & Diabetes 109, S57.

Gilmore, W., Weiner, L.P. & Correale, J. Effect of estradiol on cytokine secretion by proteolipid protein-specific Tcell clones isolated from multiple sclerosis patients and normal control subjects. Journal of Immunology 1997; 158:446-51.

Hall G.M.; Daniels M; Huskisson E.C.; Spector T.D. "A randomised controlled trial of the effect of hormone replacement therapy on disease activity in postmenopausal rheumatoid arthritis." Annals of the Rheumatic Diseases, Feb. 1994, 53(2):112-6. Pub type: Clinical Trial; Journal Article; Randomized Controlled Trial.

Harms, C., Lautenschlager, M., Bergk, A. et al. "Differential mechanisms of neuroprotection by 17 beta-estradiol in apoptotic versus necrotic neurodegeneration." J Neurosci 2001; 21 : 2600-9.

Hernan M.A.; Hohol M.J.; Olek M.J.; Spiegelman D.; Ascherio A. "Oral contraceptives and the incidence of multiple sclerosis." Neurology, Sep. 26, 2000, 55(6):848-54.

Hill, J.A., Polgar, K., Anderson, D.J., "T-Helper I-Type Immunity to Trophoblast in Women with Recurrent Spontaneous Abortion," JAMA, 273:1933-1936,1995.

Hofbauer, R. et al. "Oral Contraceptives that Contain Ethinyl Estradiol (0.035 mg) and Cyproterone Acetate (2 mg) inhibit Leukocyte Transmigration through Endothelial Cell Monolayers," Fertility & Sterility, vol. 72, No. 4, Oct. 1999, p. 652-656.

Hunter, S.F., Weinshenker, 8.G., Carter, J.L. and Noseworthy, J.H., "Rational Clinical Immunotherapy for Multiple Sclerosis," Mayo Clinic Proceedings, 72(8):765-80, Aug. 1997.

Ito A.; Bebo B.F. Jr.; Matejuk A; Zamora A; Silverman M; Fyfe-Johnson A; Offner H. "Estrogen treatment down-regulates TNF-alpha production and reduces the severity of experimental autoimmune encephalomyelitis in cytokine knockout mice." Journal of Immunology, Jul. 2001, 167(1):542-52.

Jacobs, L.D., Beck, R.W., Simon, J.H. et al. "Intramuscular interferon beta-1a therapy initiated during a first demyelinating event in multiple sclerosis." Champs Study Group. N Engl J Med 2000; 343:898-904.

Janeway, C.A. and Bottomly, K., "Signals and Signs for Lymphocyte Responses," Cell, 576:275-285, 1994.

Jansson, L. & Holmdahl, R. "Oestrogen induced suppression of collagen arthritis. IV: Progesterone alone does not affect the course of arthritis but enhances the oestrogen-mediated therapeutic effect." Journal of Reproductive Immunology 1989; 15:141-50.

Jansson, L., A. Mattsson, R. Mattsson, and R. Holmdahl. 1990. "Estrogen induced suppression of collagen arthritis. V: Physiological level of estrogen in DBAII mice is therapeutic on established arthritis, suppresses anti-type II collagen T-cell dependent immunity and stimulates polyclonal B-cell activity." Journal of Autoimmunity 3:257.

Jensen, J., Krakauer, M. & Sellebjerg, F., "Increased T Cell Expression of COI 54 (CD40-Ligand) in Multiple Sclerosis," European Journal of Neurology, 2001; 8:321-8.

Kassi, E.N., Vlachoyiannopoulos, P.G., Moutsopoulos, H.M. et al. "Molecular analysis of estrogen receptor alpha and beta in lupus patients." Eur J Clin Invest 200 I; 31: 86-93.

Katzenellenbogen, B., "Biology and Receptor Interactions of Estriol and Estriol Derivatives in vitro and in vivo," The Journal of Steroid Biochemistry, 20:1033-1037,1984.

Kennedy, M.K., Torrance, D.S., Picha, K.S. and Mohier, K.M., "Analysis of Cytokine mRNA Expression in the Central Nervous System of Mice With Experimental autoimmune Encephalomyelitis Reveals that IL-10 mRNA Expression Correlates with Recovery," J. Immunol., 149:2496-2505, 1992.

Kent, Fukaura, Pietrusewicz, Khoury, Weiner, Hatler, "Oral Administration of Myelin Induces Antigen-Specific TGF-beta I-Secreting T Cells in Multiple Sclerosis Patients," Annals of the New York Academy of Sciences, 815:412-422, Apr. 5, 1997.

Kim, Sookhyun; Dalai, Mira; Voskuhl, Rhonda R. "Mechanisms in the shift toward TH2 during pregnancy: A role for estriol treatment of TH1 mediated disease." Annual Meeting of the Professional Research Scientists on Experimental Biology 98, Part I San Francisco, California, USA Apr. 18-22, 1998. FASEB Journal. Mar. 17, 1998. 12(4):A616.

Kirkengen, A.L., Andersen, P., Gjersoe, E., Johannessen, G.R., Johnsen, N. and Bodd, E., "Oestriol in the Prophylactic Treatment of Recurrent Urinary Tract Infections in Postmenopausal Women," Scan. J. Prim. Health Care, 10: 139-142, 1992.

Paty, D. W. & Li, O.K. Interferon beta-I b is effective in relapsing-remitting multiple sclerosis. II. MRI analysis results of a multicenter,

(56) References Cited

OTHER PUBLICATIONS randomized, double-blind, placebo-controlled trial. UBC MSIMRI Study Group and the IFNB Multiple Sclerosis Study Group. Neurology 1993; 43:662-7.

Kozovska, M.E., Hong, J., Zang, Y.C. et al. "Interferon beta induces T-helper 2 immune deviation in MS." Neurology 1999; 53: 1692-7.

Krishnan, L., Guilbert, L.J., Wegmann, T.G., Belosevic, M., Mosmann, T.R., "T-Helper I Response Against Leishmania Major in Pregnant C57BL/6 Mice Increases Implantation Failure and Fetal Reabsorptions: Correlation with Increased IFN and TNF and Reduced IL-IO Production by Placental Cells," J. Immunol., 156:653-662, 1996.

Kuchroo, V.K., Martin, C.A., Greer, J.M., Ju, S., Sobel, R.A. and Steinman, L., "Cytokines and Adhesion Molecules Contribute to the Ability of Myelin Proteolipid Protein-Specific T Cell Clones to Mediate Experimental Allergic Encephalomyelitis," J Immunol, 151:4371-4382, 1993.

Lauritzen, C. "Results of a 5 years prospective study of estriol succinate treatment in patients with climacteric complaints." Hormone and Metabolic Research 1987; 19:579-84.

Lauritzen, C., "The Female Climacteric Syndrome: Significance, Problems, Treatment," Acta Obstet. Gynecol. Scand., 51 (suppl):49-6I, 1976.

Lauritzen, C., "The Management of the Premenopausal and the Postmenopausal Patient," Front. Horm. Res., 2:2-21, 1973.

Lemon, H.M., "Estriol Prevention of Mammary Carcinoma Induced by 7,12-dimethylbenzanthracene and Procarbazine," Cancer Research, 35:1341-1353,1975.

Lemon, H.M., "Oestriol and Prevention of Breast Cancer," Lancet, 1:547, 1973.

Li, D.K. Zhao, GJ. & Paty, D.W. "Randomized controlled trial of interferon-beta-1a in secondary progressive MS: MRI results." Neurology 2001; 56: 1505-13.

Lin, H., Mosmann, T.R., Guilbert, L., Tuntipopipat, S. and Wegmann, T.G., "Synthesis of T Helper 2-Type Cytokines at the Maternal-Fetal Interface," J. Immunol., 151:4562-4573, 1993.

Live, S.M. & Voskuhl, R.R. "Testosterone acts directly on CD4+ T-lymphocytes to increase ILIO production." Journal of Immunology 2001; 167:2060-2067.

Martin, R., McFarland, H.F. & McFarlin, D.E., "Immunological Aspects of Demyelinating Diseases," Annual Review of Immunology, 10: 1534-87, 1992.

Marzi, M., Vigano, A., Trabattoni, D., Villa, M.L., Salvaggio, A., Clerici E. and Clerici M., "Characterization of Type 1 and Type 2 Cytokine Production Profile in Physiologic and Pathologic Pregnancy," Clin. Eltp. Immunol., 106: 127-133, 1996.

Matejuk, A., Adlard, K., Zamora, A. et al. "17beta-estradiol inhibits cytokine, chemokine, and chemokine receptor mRNA expression in the central nervous system of female mice with experimental autoimmune encephalomyelitis." J Neurosci Res 2001; 65:529-42.

McDonald, W.I et al., (2001) "Recommended Diagnostic Criteria for Multiple Sclerosis: Guidelines from the International Panel on the Diagnostic of Multiple Sclerosis." Ann Neurol 50, 121-7.

McFarland, H.F., Frank, J.A., Albert, P.S., Smith, M.E., Martin, R., Harris, J.D., Patron as, N., Maloni, H., McFarlin, D.E., "Using Gadolinium-Enhanced Magnetic Resonance Imaging Lesions to Monitor Disease Activity in Multiple Sclerosis," Ann. Neurol., 32:758-766, 1992.

Miller, D.H., Albert, P.S., Barkhof, F., Francis, G., Frank, J.A., Hodgkinson, S., Lubl in, F.D., Paty, D.W., Reingold, S.C., Simon, J., "Guidelines for the Use of Magnetic Resonance Techniques in Monitoring the Treatment of Multiple Sclerosis," Annals of Neurology, 39:6-16, 1996.

Milner, R., "Understanding the Molecular Basis of Cell Migration; Implications for Clinical Therapy in Multiple Sclerosis," Clinical Science, 92(2):113-22, Feb. 1997.

Minaguchi, H., et al., "Effect of Estriol on Bone Loss in Postmenopausal Japanese Women: A Multicenter Prospective Open Study," Journal of Obstetrics and Gynaecology Research, 22(3):259-65, Jun. 1996.

Mosselman, S., Polman, J. & Dijkema, R. "ER beta: identification and characterization of a novel human estrogen receptor." FEBS Lett 1996; 392:49-53.

Murray, J.S., Ferrandis-Edwards, D., Wolfe, CJ. and Schountz, T., "Major Histocompatibility Complex Regulation of T Helper Functions Mapped to a Peptide C Terminus that Controls Ligand Density," Eur. J. Immunol., 24:2337-2344, 1994.

Nelson, J.L., Hughes, K.A., Smith, A.G., et al., "Remission of Rheumatoid Arthritis During Pregnancy and Maternal-Fetal Class II Alloantigen Disparity," American Journal of Reproductive Immunology, 1992; 28:226-7.

Nelson, J.L., Hughes, K.A., Smith, A.G., Nisperos, B.B., Branchaud, A.M., and Hansen, J.A., "Maternal-Fetal Disparity in HLA Class II Alloantigens and the Pregnancy-Induced Amelioration of Rheumatoid Arthritis," N. Eng. J. Med, 329:466-471, 1993.

Nishibe, A., Morimoto, S., Hirota, K., Yasuda, O., Ikegami, H., Yamamoto, T., Fukuo, K., Onishi, T. and Ogihara, T., "Effect of Estriol and Bone Mineral Density of Lumbar Vertebrae in Elderly and Postmenopausal Women", Japanese Journal of Geriatrics, 33(5):353-9, May 1996.

Noelle, RJ. "CD40 and its Ligand in Host Defense," Immunity, 4:415-419, 1996.

Lee, S.J. et al. "Neurotrophic and neuroprotective actions of estrogens and their therapeutic implications." Annu Rev. Pharmacol Toxicol 2001, vol. 41 : pp. 569-591.

Leranth, C. et al. "Estrogen is essential for maintaining nigrostriatal dopamine neurons in primates: Implications for Parkinson's disease and memory." J. Neurosci 2000, vol. 20: pp. 8604-8609.

Maki, P.M. et al. "Enhanced verbal memory in nondemented elderly women receiving hormone-replacement therapy." Am J. Psychiatry 2001, vol. 158: pp. 227-233.

Maki, P.M. et al. "Implicit memory varies across the menstrual cycle: Estrogen effects in young women." Neuropsychologia 2002, vol. 40: pp. 518-529.

Murphy, D.O. et al. "Estradiol increases dendritic spine density by reducing GABA neurotransmission in hippocampal neurons." J. Neurosci 1998, vol. 18: pp. 2550-2559.

Rice, M.M. et al. "Postmenopausal estrogen and estrogen-progestin use and 2-year rate of cognitive change in a cohort of older Japanese American women: The Kame Project." Arch Intern Med. 2000, vol. 160: pp. 1641-1649.

Rudick, R.A. et al. "Use of the brain parenchymal fraction to measure whole brain atrophy in relapsing-remitting MS. Multiple Sclerosis Collaborative Research Group." Neurology, 1999, vol. 53, pp. 1698-1704.

Sicotte, N.L. et al. "Treatment of multiple sclerosis with the pregnancy hormone estriol." Ann. Neurology, 2002, vol. 52: pp. 421-428.

Van Vollenhoven, R.F. et al. "Estrogen, progesterone, and testosterone: Can they be used to treat autoimmune diseases?" Cleveland Clinic Journal of Medicine, 1994, vol. 61: pp. 276-284.

Vanderhorst, V.G. et al. "Estrogen induces axonal outgrowth in the nucleus retroambiguus-lumbosacral motoneuronal pathway in the adult female cat." J. Neurosci 1997, vol. 17: pp. 1122-1136.

Voskuhl, R.R. "Hormone-based therapies in MS." International MS Journal, vol. 10, No. 2, pp. 61-66 (2003).

Biewenga E., Cabell L., and Audesirk T., 2005, "Estradiol and raloxifene protect cultured SN4741 neurons against oxidative stress," Neurosci. Lett., v. 373, p. 179-183.

Brinton R. D., 2008, "Estrogen regulation of glucose metabolism and mitochondrial function: Therapeutic implications for prevention of Alzheimer's disease," Adv. Drug Delivery Rev., v. 60, pp. 1504-1511.

Cho J. J., Iannucci F. A., Fraile M., Franco J., Alesius T. N., and Stefano G. B., 2003, "The role of the estrogen in neuroprotection: implications for neurodegenerative diseases," Neuro. Endocrinol. Lett., v. 24, p. 141-147.

Gelinas S., Bureau G., Valastro B., Massicotte G., Cicchetti F., Chiasson K., Gagne B., Blanchet J., and Martinoli M. G., 2004, "Alpha and beta estradiol protect neuronal but not native PC12 cells from paraquat-induced oxidative stress," Neurotox. Res., v. 6, p. 141-148.

Kenchappa R. 5., Diwakar L., Annepu J. and Ravindranath V., 2004, "Estrogen and neuroprotection: higher constitutive expression of glutaredoxin in female mice offers protection against MPTP-mediated neurodegeneration," FASEB J., v. 18, p. 1102-1104.

(56) References Cited

OTHER PUBLICATIONS

Schiff, I., Wentworth, B., Koos, B. et al. "Effect of estriol administration on the hypogonadal woman." Fertility and Sterility 1978; 30:278-82.

Kishi Y., Takahashi J., Koyanagi M., Morizane A, Okamoto Y., Horiguchi S., Tashiro K., Honjo T., Fujii S., and Hashimoto N., 2005, "Estrogen promotes differentiation and survival of dopaminergic neurons derived from human neural stem cells," J. Neurosci. Res., v. 79, p. 279-286.

Koloszar, S. and Kovacs, L., "Treatment of Climacteric Urogenital Disorders with an Estriol-Containing Ointment," Orvosi Hetilap, 136(7):343-5, Feb. 12, 1995.

Li R., and Shen Y., 2005, "Estrogen and brain: synthesis, function and diseases," Front. Biosci., v. 10, p. 257-267.

Quesada A, and Micevych P. E., 2004, "Estrogen interacts with the IGF-1 system to protect nigrostriatal dopamine and maintain motoric behavior after 6-hydroxdopamine lesions," J. Neurosci. Res., v. 75, p. 107-116.

Ramirez A. D., Liu X., and Menniti F. S., 2003, "Repeated estradiol treatment prevents MPTP-induced dopamine depletion in male mice," Neuroendocrinology, v. 77, p. 223-231.

Saunders-Pullman R., 2003, "Estrogens and Parkinson disease: neuroprotective, symptomatic neither, or both?" Endocrine, v. 21, p. 81-87.

Sawada H., and Shimohama S., 2003, "Estrogens and Parkinson disease: novel approach for neuroprotection," Endocrine, v. 21, p. 77-79.

Shughrue P. J., 2004, "Estrogen attenuates the MPTP-induced loss of dopamine neurons from the mouse SNc despite a lack of estrogen receptors (ERalpha and ERbeta)," Exp Neurol, v. 190, p. 468-477.

Wise P. M., 2002, Estrogens and Neuroprotection, Trends in Endocrinology & Metabolism, . v. 13, n. 6, pp. 229-230.

Ortho-Micronor. Drug Datasheet (online). Ortho-McNeil Pharmaceuticals. http://www.ortho-mcneilpharmaceutical.com/products/pi/pdfs/micro.pdf, p. 1 (1998).

Troisi et al. "Maternal Serum Oestrogen and Androgen Concentrations in Preeclamptic and Uncomplicated Pregnancies" International Journal of Epidemiology, vol. 32(3) p. 458 (Jun. 2003).

Soldan et al., "Immune Modulation in Multiple Sclerosis Patients Treated with the Pregnancy Hormone Estriol", The Journal of Immunology, vol. 171(11) p. 6267-74 (Dec. 2003).

Morissette et al. "Oestrogens Prevent Loss of Dopamine Transporter (OAT) and Vesicular Monoamine Transporter (VMAT2) in Substantia Nigra of 1-Methyl-4-Phenyl-1,2,3,6-Tetrahydropyridine Mice." Journal of Neuroendocrinology (2005) 17:509-517.

Tsang et al. "The use of estrogen in the treatment of Parkinson's disease." Parkinsonism and Related Disorders. (2001) 8:133-137.

Gomez-Mancilla et al. "Effect of estrogen and progesterone on L-DOPA induced dyskinesia in MPTP-treated monkeys." Neuroscience Letters (1992) 135:129-132.

Perrella, Joel et al. "Protection of cortical cells by equine estrogens against glutamate-induced excitotoxicity is mediated through a calcium independent mechanism". BMC Neuroscience ( 2005 ),6, No PP. Given CODEN: BNMEA6; ISSN: 1471-2202 URL: http://www.biomedcentral.com/content /pd f/14 71 -2202-6-34. pdf, May 10, 2005.

Wen, Yi et al, "Transient Cerebral Ischemia Induces Aberrant Neuronal Cell Cycle Re-entry and Alzheimer's Disease-like Tauopathy in Female Rats," Journal of Biological Chemistry (2004), 279(21), 22684-22692 CODEN: JBCHA3; ISSN: 0021-9258, Feb. 24, 2004.

Margolis K. L, et al. "Effect of oestrogen plus progestin on the incidence of diabetes in postmenopausal women: results from the Women's Health Initiative Hormone Trial." Diabetologia, vol. 47, No. 7, Jul. 2004, pp. 1175-1187.

Kumar D M et al, "Role of nonfeminizing estrogen analogues in neuroprotection of rat retinal ganglion cells against glutamate-induced cytotoxicity." Free Radical Biology and Medicine, Elsevier Science, US, vol. 38, No. 9, May 1, 2005, pp. 1152-1163.

Offner, Halina, "Neuroimmunoprotective effects of estrogen and derivatives in experimental autoimmune encephalomyelitis: Therapeutic implications for multiple sclerosis." Journal of Neuroscience Research ( 2004 ), 78(5), 603-624 CODEN: JNREDK; ISSN: 0360-4012, Oct. 28, 2004.

Jungers, P., Dougados, M., Pelissier, c., Kuttenn, K., Tron, F., Lesavre, P. and Bach, J., "Influence of Oral Contraceptive Therapy on the Activity of Systemic Lupus Erythematosus," Arthritis and Rheumatism, 25 :618-623, 1982.

Ratkay L Get Al, "Evaluation of a model for post-partum arthritis and the role of oestrogen in prevention of MRL-Ipr associated rheumatic conditions" Clinical and Experimental Immunology, vol. 98, No. 1, 1994, pp. 52-59, ISSN: 0009-9104.

El-Etr M et al: "Steroid hormones in multiple sclerosis" Journal of Neurological Sciences, Elsevier Scientific Publishing Co, Amsterdam, NL LNKD—001:10.1 016/J.JNS.2005.03.004, vol. 233, No. 1-2, Jun. 15, 2005, pp. 49-54, ISSN: 0022-51 OX.

Buyon, Jill P. et al. "The effect of combined estrogen and progesterone hormone replacement therapy on disease activity in systemic lupus erythematosus: A randomized trial." Annals of Internal Medicine, vol. 142, No. 12, Part 1. Jun. 2005, pp. 953-962.

Wilder, R. L. "Hormones, pregnancy, and autoimmune diseases." Annals of the New York Academy of Sciences May 1, 1998 LNKD-PUBMED:9629235. vol. 840, May 1, 1998, pp. 45-50.

Bebo BF Jr.; Fyfe-Johnson A; Adlard K; Beam AG; Vandenbark AA; Offiler H. "Low-dose estrogen therapy ameliorates experimental autoimmune encephalomyelitis in two different inbred mouse strains." Journal of Immunology, Feb. 1, 2001, 166(3):2080-9.

Krishnan, L., Guilbert, L.J., Russell, A.S., Wegmann, T.G., Mosmann, T.R., Belosevic, M., "Pregnancy impairs resistance of C57BL/6 Mice to Leishmania Major Infection and Causes Decreased Antigen-Specific IFN-Responses and Increased production of T Helper 2 Cytokines," J. Immunol, 156:644-652, 1996.

Mattsson, R., Mattsson, A., Holmdahl, R. et al. "Maintained pregnancy levels of oestrogen afford complete protection from post-partum exacerbation of collagen-induced arthritis." Clinical and Experimental Immunology 1991; 85:41-7.

* cited by examiner

Pretreatment　　　Estriol Treatment　　Post Treatment　　Estriol Treatment
I I I*+I I I*　　 I I I*I I I*+　　  I I I*I I I*　　 I I I I*
months 1-6　　　 months 7-12　　　 months 13-18　　months 19-22

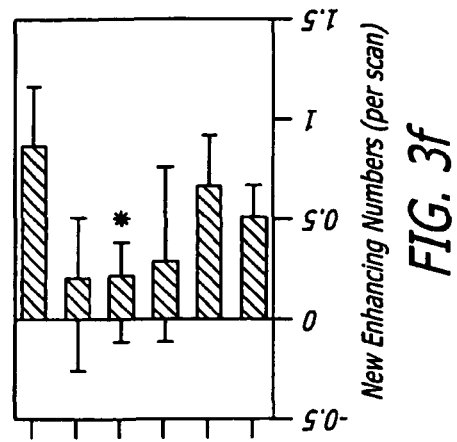
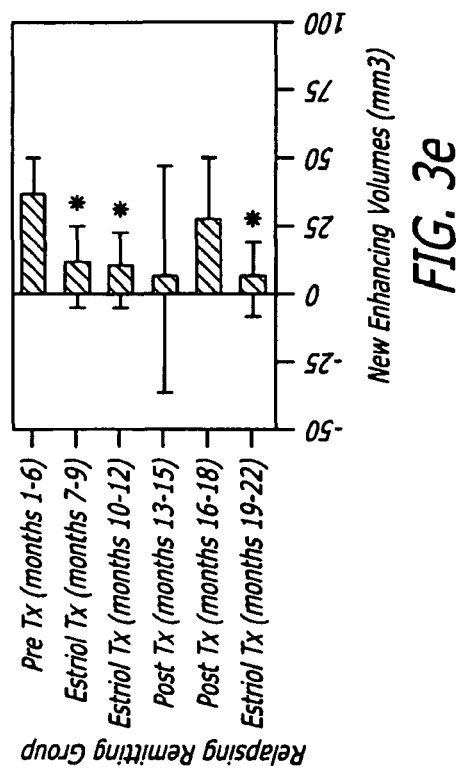
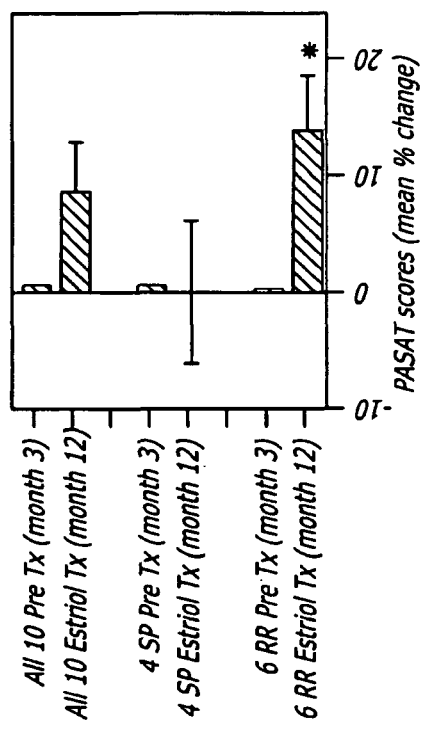

PREGNANCY HORMONE COMBINATION FOR TREATMENT OF AUTOIMMUNE DISEASES

CROSS-REFERENCE TO RELATED APPLICATIONS

This application claims priority from International Patent Application No. PCT/US2008/007065, filed Jun. 4, 2008, which claims priority to U.S. Provisional Patent Application No. 60/933,030, filed Jun. 4, 2007, both of which are incorporated by reference herein.

This application is a Continuation-In-Part Application of U.S. patent application Ser. No. 11/151,040, filed on Jun. 13, 2005, which is a continuation of application Ser. No. 10/131,834, filed on Apr. 24, 2002 and issued as U.S. Pat. No. 6,936,599, which in turn claims priority to Provisional Application No. 60/286,842, filed on Apr. 25, 2001.

BACKGROUND OF THE INVENTION

1. Field of the Invention

This invention relates generally to therapies for treating autoimmune diseases and, more particularly, to administering primary agents being estrogens or estrogen receptor active agents for the treatment of cell mediated diseases. In combination, secondary agents which effect the immune system are also administered. Finally, treatment kits are provided containing at least one primary agent and at least one secondary agent for treating a patient presenting with symptomology of an autoimmune disease.

More specifically, the present invention may comprise a combination of a pregnancy hormone (such as estriol), combined with a gestagen (such as levonorgestrel or norethindrone) for treating autoimmune diseases. The combination may be useful at least for the continuous treatment and prevention of relapses in patients having an autoimmune disease, such as multiple sclerosis, obviating the need for pregnancy hormone therapy holidays for menstruation that may be associated with higher rates of relapse of disease during such holiday.

2. General Background and State of the Art

There is a distinct female preponderance of autoimmune diseases during the reproductive ages including multiple sclerosis (MS), rheumatoid arthritis (RA), uveitis, myesthenia gravis (MG), Sjogren's syndrome, Hashimoto's thyroiditis, psoriasis, and lupus.

For example, MS is a chronic, and often debilitating disease affecting the central nervous system (brain and spinal cord). MS affects more than 1 million people worldwide and is the most common neurological disease among young adults, particularly woman. The exact cause of MS is still unknown. MS attacks the nervous system resulting in myelin sheaths surrounding neuronal axons to be destroyed. This demyelinization can cause weakness, impaired vision, loss of balance, and poor muscle coordination. MS can have different patterns, sometimes leaving patients relatively well after episodes of acute worsening, sometimes leading to progressive disability that persists after episodes of worsening. In the worst cases the disease can lead to paralysis or blindness.

Steroid hormones or sex-linked gene inheritance may be responsible for the enhanced susceptibility of women to these autoimmune diseases. A role for steroid hormones in susceptibility to autoimmune disease is supported by observations of alternations in disease symptomatology, with alterations in sex hormone levels such as during pregnancy. For example, women with MS, RA and psoriasis have been reported to experience remission of symptoms during late gestation. Particularly, MS patients have been reported to show a decrease in relapse rate in pregnancy.

Normally, cell-mediated immunity is mediated by T helper cell (Th1) secretion of interferon gamma (IFN-γ) and tumor necrosis factor beta (TNF-β). In contrast, humoral immunity is mediated by another group of T helper cells (Th2) secreting interleukin (IL)-10, IL-4, IL-5 and IL-6. A systemic shift toward humoral immunity (or Th2-mediated immunity) has been noted during pregnancy. During pregnancy, cell-mediated immunity is decreased and humoral-mediated immunity is increased thereby promoting fetal survival. Thus, this systemic shift in the immune system may explain why cell-mediated diseases, including MS, RA and psoriasis have been reported to improve during pregnancy.

Although a shift toward humoral-mediated immunity has been demonstrated during human pregnancy, mechanisms which induce this shift remain unclear. One possibility is local production of Th2 (or humoral mediated) cytokines by the placenta. Another possibility is the production of Th2 cytokines by immune cells, consequent to changed levels of steroid hormones during pregnancy. Consistent with the latter possibility, in vitro studies have demonstrated the ability of the steroid progesterone to increase IL-4 production and the ability of the steroid 17β-estradiol to increase IL-10 production during T-lymphocyte responses. However, it remains unclear what cellular mechanisms are involved in regulating in vivo amelioration of autoimmune symptomology.

Examples of potential candidates which effect may effect MS during pregnancy include: Sex hormones (estrogens, progesterone), cortisol, vitamin D, alpha-fetoprotein, human chorionic gonadotropin and pregnancy specific glycoproteins.

Further, some studies have suggested that a unique pregnancy factor termed "early pregnancy factor" is responsible for improved progression of cell-mediated autoimmune diseases during pregnancy. Other studies have suggested a role for microchimerism. Still others suggest a role for local factors such as TGFβ or estriol (E3) which is known to be produced by the placenta during pregnancy. Of note, estriol is at its highest serum levels in the third trimester of pregnancy. However, estriol's role in ameliorating symptoms of autoimmune diseases in humans is unclear.

Studies in laboratory animals have established that experimental autoimmune encephalomyelitis (EAE) and other Th1 (cell-mediated) autoimmune diseases in mice improve during pregnancy.

Specifically, treatment with late pregnancy levels of estriol or supraphysiological doses of estradiol (5 times pregnancy levels) were shown to delay the onset of clinical EAE after disease was experimentally induced by immunization of mice (Jansson, et al., 1994). However, there was no investigation as to how estrogens delayed the day of onset of disease, nor as to whether disease severity was effected in these animals once symptomology occurred.

In another study, it was shown that EAE disease severity could be reduced by treatment with estriol, either before or after disease onset. Treatment of EAE mice with 90 day release pellets of 5 milligrams or 15 milligrams of estriol was shown not only to decrease disease severity but also to enhance autoantigen specific humoral-immunity, increase production of the Th2 cytokine IL-10 and reduced inflammation and demyelination in EAE mice. Importantly, these changes in the disease were induced by a dose (5 mg) which was shown to yield estriol levels in serum that were similar to those which occur during late pregnancy (Kim, et al., Neurology, 50 (4 Supp. 4):A242-245, April 1998, FASEB Journal 12(4):A616, March 1998 and Neurology 52(6):1230-1238, April 1999; herein incorporated by reference). Thus, these results suggested that steroid hormones, and estriol in particular, may be involved in the amelioration of autoimmune reactions in the EAE animal model.

Other groups later demonstrated that estrogen potentiated the effects of treatment with TCR proteins to reduce autoimmune reactions in EAE mice. Offner, et al., *FASEB Journal* 14(6):A1246, April 2000; Int. Journal of Mol. Medicine 6 (Supp. 1): S8, October 2000 and Journal of Clin. Invest. 105(10):1465-1472, May 2000). Further, it was shown in animal studies that estrogen suppressed the onset EAE in mice (Ito, et al., *Journal of Immunology*, 167(1): 452-52, 2001) and that presumed diestrus levels of estrogens reduced some manifestations of active EAE in mice. (Bebo, et al., *Journal of Immunology* 166(3): 2080-9, 2001.)

However, the etiology and disease progression of EAE and MS are not identical, thus it is unclear that estrogens alone would be effective in ameliorating autoimmune responses in human patients. Indeed, not only is it unknown whether pregnancy doses of estrogens might be protective in humans with autoimmune disease, it is unclear even in mice whether low doses of estrogens are protective. For example, it has been reported by some that ovariectomy of female mice makes EAE disease worse (Matejuk, et al., 2001), while others have found that ovariectomy had no effect on disease severity (Kim, et al., 2001; Voskuhl and Palaszynski, 2001a; Voskuhl and Palaszynski, 2001b). Thus, it is controversial whether low levels of estrogens, as they exist during the menstrual cycle, are protective even in mice.

Data from human studies to date have shown no clear benefit of hormones in treating any autoimmune disease. In humans, administration of available hormone therapies (including HRTs and OCPs) containing a mixture of sex hormones cause some autoimmune diseases to improve while others worsen.

For example, there has been no conclusive evidence that women are protected from or have a decrease in symptomology or relapse rates due to sex steroids. One study noted that past use of oral contraceptives in healthy women had no effect on subsequent risk to develop MS (Hernan, et al., 2000). Further, another study found that the incidence rates for MS in current users were not decreased as compared to never-users (Thorogood and Hannaford, 1998). Thus, low doses of estrogens in oral contraceptives are not of sufficient type or dose to ameliorate the immunopathogenesis of MS even temporarily during intercurrent use. At best, in one study, patients had the subjective impression that pre-existing MS symptoms (as opposed to relapse rates) worsen during the premenstrual period and that the use of oral contraceptives may have decreased this worsening (Zorgdrager and De Keyser, 1997). Importantly, the lack of reports of an effect of oral contraceptive therapy on MS relapses is in marked contrast to what has been observed during pregnancy.

In contrast, it has been shown that women had a lower risk of developing MS during pregnancy compared to non-pregnant states (Runmarker and Andersen, 1995). Due to the numerous changes that occur during pregnancy, hormonal and nonhormonal (as listed above), the etiology of the beneficial effect of pregnancy may or may not be related to sex steroid fluctuations. It has also been reported for decades that pregnancy decreases MS relapses (Abramsky, 1994; Birk, et al., 1990; Birk, et al., 1998; Damek and Shuster, 1997; Runmarker and Andersen, 1995; Confavreux, et al., 1998). These studies have shown that the latter part of pregnancy is associated with a significant reduction in relapses, while there is a rebound increase in relapses post partum. In contrast, the absence of such an effect on relapses during OCP or HRT indicate that low level sex steroids are not adequate to treat these symptoms.

Further, women having rheumatoid arthritis that were treated with HRT did not show significant improvement in their symptomology. (DaSilva and Hall, *Baillieres Clinical Rheumatology* 1992, 6:196-219; Bijlsma, et al., *Journal of Repro. Imm.* 28(3-4):231-4, 1992; Hall, et al., *Annals of the Rheumatic Diseases*, 53(2): 112-6, 1994.)

Thus, the low doses of hormones found naturally during the menstrual cycle or in ORT and HRT have not been shown to be effective at ameliorating the symptomology of autoimmune diseases. This is in spite of the observation that women having MS have a decreased relapse rate during late pregnancy. Thus, a challenge has been to identify a hormone and a treatment dose that is therapeutic in treating particular autoimmune diseases, while minimizing undesirable side effects. Obviously, the dose and method of administration of steroids in humans differs from steroid treatment in laboratory animals due to toxic effects of prolonged exposure by patients to steroid hormones. In particular, there are clinical concerns of inducing breast or endometrial cancers in women requiring long term exposure to steroid hormones.

Although not available in the United States, the pregnancy hormone estriol has been recently prescribed in Europe and Asia largely as an HRT for postmenopausal women. On the other hand, hormonal contraceptives have been widely prescribed for premenopausal and perimenopausal women since the 1960's. Since that time, a number of hormonal components have been investigated as to their suitability for administration. A fundamental subdivision into combination and sequential contraceptive products is possible.

For example, if the desired cycle time is 28 days (in the case of the known combination products) administration takes place over 21 days in a constant or varying absolute and/or relative dosage of a combination of an estrogen and a gestagen, in which the estrogen product can, for example, be natural estrogen or synthetic ethinyl estradiol. The taking of the 21 daily units is followed by a seven-day interval where there is a withdrawal bleeding simulating natural menstruation.

In the known sequential products, for a desired cycle time of 28 days, administration takes place for 7 days of a pure estrogen product and then for 15 days of a combination of an estrogen product and a gestagen product, followed by a taking-free period of, for example, 6 days when withdrawal bleeding occurs. It is known to bridge the taking-intervals of combination and sequential products to administer placebos. However, it has been assumed that during the roughly one-week placebo interval no hormones should be administered, in order to ensure a reliable withdrawal bleeding.

Only in the case of substitution products in the menopause of older women have hormones been administered continuously throughout the cycle, for example, in the sequence 10 days estrogen product, 11 days combination of estrogen and gestagen product, 7 days estrogen product in a particularly low dosage.

German Patent No. 43 08 406 discloses a combination contraceptive product for premenopausal women, which comprises one or more stages. At least one stage contains the combination of three components, namely a biogenous estrogen, a synthetic estrogen and a gestagen and the further stages in each case comprise a placebo or a biogenous or synthetic gestagen, or a biogenous or synthetic estrogen, or a combination of two components, namely a biogenous estrogen, a synthetic estrogen and a gestagen or a combination of synthetic estrogen and a gestagen.

U.S. patent application Ser. No. 10/867,954 filed by Hesch published Dec. 2, 2004 and assigned to Wyeth Pharmaceuticals, Inc. describes estrogens and gestagens as combination products for continuous hormonal contraception in premenopausal women, but does not describe their use for autoimmune disease. Furthermore, although estriol is mentioned as an estrogen in this patent application, the preferred embodiment contemplates the use estradiol, which is not pregnancy hormone, and utility of which has been clinically proven to be ineffective for the treatment of autoimmune diseases (such as MS).

The description above makes it clear that in the stage concept there is typically a change of state over the period of time. Such a state change can take place in that the composition of the phases forming the stage is modified with respect to the components used and in that only the concentrations of the components used in the phases forming the stage undergo changes.

Consequently, there are no hormone combinations identified for safe and effective use to delay and/or treat autoimmune diseases, and for potential continuous therapies.

INVENTION SUMMARY

A general object of the present invention is to provide a method of administering hormones to mammals to treat autoimmune related diseases, more particularly, Th1-mediated (cell-mediated) autoimmune diseases including: multiple sclerosis (MS), rheumatoid arthritis (RA), psoriasis, autoimmune thyroiditis, uveitis and other autoimmune diseases in which clinical symptomology has shown improvement during the third term of pregnancy.

In accordance with one aspect of the present invention, these objectives are accomplished by providing a treatment for autoimmune related diseases with a selected dose and course (including a continuous course) of a primary agent being an estrogen or estrogen receptor-effective composition, such as estriol.

In accordance with one aspect of the present invention, these objectives are accomplished by providing a patient with a therapeutically effective amount of estriol, comprising from about 1 to 20 milligrams per day, about 5 to 10 milligrams per day or more specifically, about 8 milligrams once daily via oral administration.

In accordance with another aspect of the present invention, these objectives are accomplished by providing a therapeutically effective amount of a primary agent in combination with a therapeutically effective amount of a secondary active agent, such as a gestagen (such as levonorgestrel or norethindrone).

The combination of agents in a continuous administration course may be useful at least to delay the onset of, prevent or delay relapse or treat patients exhibiting symptoms of an autoimmune disease, such as multiple sclerosis. Further, the combination may obviate the need for pregnancy hormone therapy holidays for menstruation that may be associated with higher rates of relapse of disease during such holiday.

In one embodiment, the present invention may comprise a product comprising and/or method of treatment containing a daily dosage amount of estriol and constant or varied dosages of a gestagen that is useful for delaying the onset, preventing relapses, and/or treating the symptoms of autoimmune disease, such as, multiple sclerosis, psoriasis, myesthania gravis, rheumatoid arthritis, uveitis, Sjogren's syndrome, or Hashimoto's thyroiditis and lupus.

In one embodiment of the invention, the method of treatment may provide a continuous, combined administration of a first hormonal component comprising at least one estrogen and a second hormonal component comprising at least one gestagen.

In one embodiment of the invention, the estrogen as the first hormonal component can be selected from the group comprising synthetic estrogens, biogenous estrogens, antiestrogens and hormonal analogs with estrogen or antiestrogen action. In one embodiment, the synthetic estrogen is estriol.

According to one embodiment of the invention, the biogenous estrogen may be selected from the group comprising estradiol, estriol, estrone, estrane, etc., as well as hormonal compounds rapidly splitting off at least one biogenous estrogen after taking. According to one embodiment the estradiol comprises 17-α-estradiol and/or 17-β-estradiol. According to another embodiment, the daily administered biogenous estrogen quantity in the case of estradiol, particularly α and β-estradiol, is 0.1 to 2 mg and in the case of conjugate estrogens 0.05 to 0.5 mg.

According to another embodiment, the gestagen as the secondary agent may be chosen from the group comprising: progesterone, chlormadinone acetate, norethisterone acetate, norethindrone, cyproterone acetate, desogestrel, levonorgestrel, other natural and/or synthetic gestagens, antigestagens and hormonal analogs with gestagen or antigestagen action, as well as hormonal compounds which rapidly split off at least one gestagen following taking.

In one embodiment, the daily units comprising both hormonal components, are placed in spatially separated and individually removable manner in a packaging unit. In one embodiment the daily units of both hormonal components may be placed in the packaging unit separately, but when administered together form the desired combination.

In one embodiment, the combination may be administered orally. In one embodiment, the combination may be administered transdermally. In one embodiment, the combination may be administered intravaginally. In one embodiment, the combination may be in depot injection form. In one embodiment, the combination may be administered as a hormonal implant.

In another embodiment of the method according to the invention, the composition(s) according to the invention is administered to a subject.

The above described and many other features and attendant advantages of the present invention will become apparent from a consideration of the following detailed description when considered in conjunction with the accompanying drawings.

BRIEF DESCRIPTION OF THE DRAWINGS

FIG. 3a-f are bar graphs depicting each patient's gadolinium enhancing lesion volumes on serial cerebral MRIs which were assessed at each month during the pretreatment, estriol treatment and post treatment periods.

FIG. 4 is a bar graph depicting mean percent change in PASAT scores during treatment with estriol as compared to pretreatment.

DETAILED DESCRIPTION OF THE PREFERRED EMBODIMENTS

Figures 1A, 1B:
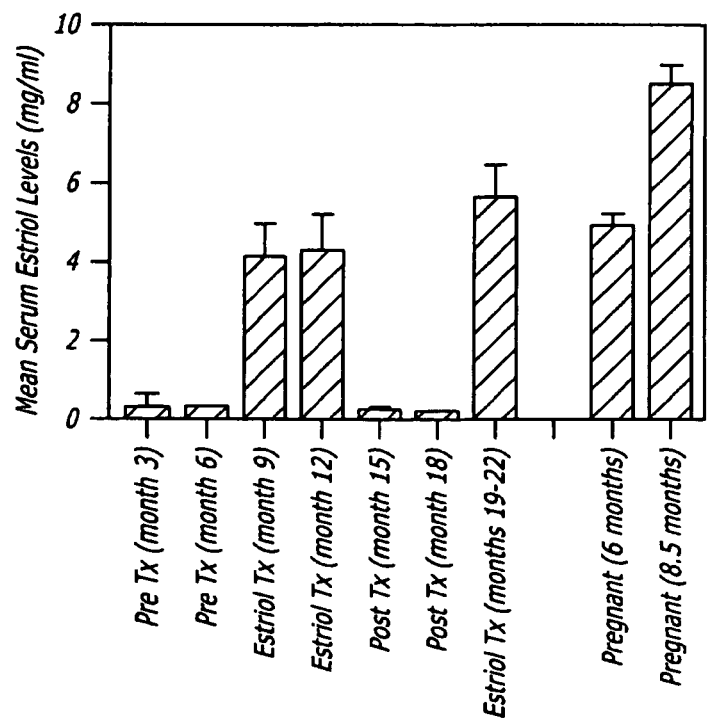
FIG. 1a is a schematic depicting the trial design described in Example 1.
FIG. 1b is a bar graph depicting human serum levels during pregnancy, estriol treatment (Tx), and pretreatment (Pre Tx levels).

This description is not to be taken in a limiting sense, but is made merely for the purpose of illustrating the general principles of the invention. The section titles and overall organization of the present detailed description are for the purpose of convenience only and are not intended to limit the present invention.

Generally, the invention involves a method of treating mammal exhibiting clinical symptoms of an autoimmune disease comprising administering a primary agent and a secondary agent at therapeutically effective dosages in an effective dosage form at a selected interval. The treatment is aimed at reducing the rate of onset, degree of symptomology and/or progression of autoimmune disease. In the preferred embodiment of the invention, human patients clinically diagnosed with MS (including both relapsing remitting or secondary progressive type patients) are treated with the combination of an estrogen and at least one gestagen.

Amelioration of the symptomology or reduced progression of the autoimmune disease refers to any observable beneficial effect of the treatment. The beneficial effect can be evidenced by a delayed onset or progression of disease symptomology, a reduction in the severity of some or all of the clinical symptoms, or an improvement in the overall health.

For example, patients who have clinical symptoms of an autoimmune disease often suffer from some or all of the following symptoms: worsening of pre-existing symptoms (such as joint pain in rheumatoid arthritis), the appearance of new symptoms (new joints affected in rheumatoid arthritis) or increased generalized weakness and fatigue. MS patients in particular suffer from the following symptoms: weakness, numbness, tingling, loss of vision, memory difficulty and extreme fatigue. Thus, an amelioration of disease in MS would include a reduction in the frequency or severity of onset of weakness, numbness, tingling, loss of vision, memory difficulty and extreme fatigue. On imaging of the brain (MRI) amelioration or reduced progression of disease would be evidenced by a decrease in the number or volume of gadolinium enhancing lesions, a stabilization or slowing of the accumulation of T2 lesions and/or a slowing in the rate of atrophy formation. Immunologically, an increase in Th2 cytokines (such as IL-10) a decrease in Th1 cytokines (such as interferon gamma) would be associated with disease amelioration.

Patients may also express criteria indicating they are at risk for developing autoimmune diseases. These patients may be preventatively treated to delay the onset of clinical symptomology. More specifically, patients who present initially with clinically isolated syndromes (CIS) may be treated using the treatment paradigm outlined in this invention. These patients have had at least one clinical event consistent with MS, but have not met full criteria for MS diagnosis since the definite diagnosis requires more than one clinical event at another time (McDonald et al., 2001). Treatment of the present invention would be advantageous at least in preventing or delaying the development of clinically definite MS.

PRIMARY AGENT. The primary agent useful in this invention is a hormone, more particularly an estrogen or a steroidal or non-steroidal estrogen receptor active agent. The primary agent may be estriol (estra-1,3,5(10)-triene-3,16,17-triol, E3), such as estriol succinate, estriol dihexanate or estriol sulfmate. However, the primary agent may be a precursor or analog of estriol (such as nyestriol), estrone (E1) or precursors or analogs of estrone, 17α-estradiol, 17β-estradiol (E2) or precursors (including aromatizable testosterone) or analogs of 17 β-estradiol.

The primary agent may also be a metabolite or derivatives of E1, E2 or E3 which are active at the estrogen receptor α or β. Metabolites and derivatives may have a similar core structure to E1, E2 or E3 but may have one or more different groups (ex. hydroxyl, ketone, halide, etc.) at one or more ring positions. Synthetic steroids which are effective at estrogen receptor are also useful in this invention, such as those described in WO 97/08188 or U.S. Pat. No. 6,043,236 to Brattsand, incorporated herein by reference.

The primary agent may also be an estrogen receptor α or β, agonists and/or antagonist. These agonists or antagonists may be steroidal or non-steroidal agents which bind to and/or cause a change in activity or binding of at least one of the estrogen receptor α or β subtypes. For example, specific agonists of ER α and ER β may be useful in this invention (Fritzmeier, et al.). Doses of these agonists may be titrated to achieve an effect on disease similar to that which is observed during pregnancy and during treatment with pregnancy doses of estriol by methodologies known to those skilled in the art of steroid pharmacology.

Any one or combination of these estrogens or estrogen receptor active agents may be used. The selection of the estrogens or estrogen receptor active agents can be made considering secondary side effects of the treatment to the patient. For example, estriol may be selected over 17β-estradiol, because estriol causes minimal endometrial proliferation and is not associated with increased risk of breast cancer. Minimal endometrial proliferation is observed when the long-acting estriol derivative, nyestriol is used. Indeed, because estriol has partial antagonist action on the binding of 17β-estradiol to the estrogen receptor in vivo, estriol was at one point in the past considered as a therapeutic agent for treatment and prevention of breast cancer.

THERAPEUTICALLY EFFECTIVE DOSAGE OF THE PRIMARY AGENT. A therapeutically effective dose of the primary agent is one sufficient to raise the serum concentration above basal levels, and preferably to pregnancy levels or above pregnancy levels. Most preferably, the therapeutically effective dosage of the primary agent is selected to result in serum levels in a patient equivalent to the steroid hormone level of that agent in women in the second or third trimester of pregnancy.

For example, during the normal female menstrual cycle estradiol levels are in the range of about 350 pg/ml serum. During pregnancy, there is about a 100 fold increase in the level of estradiol to about 10,000 to about 35,000 pg/ml serum. (Correale, et al., *Journal of Immunology*, 161:3365 (1998) and Gilmore, et al., *Journal of Immunology*, 158:446.) In contrast, estriol levels are undetectable during the menstrual cycle in the non-pregnant state. Estradiol levels rise progressively during pregnancy to levels from 3,000 to 30,000 pg/ml (3 to 30 ng/ml) (www.il-st-acad-sci.org/steroid1.html#se3t).

In one embodiment, where the primary agent is estriol, the preferable dose is from about 1 to 20 milligrams daily, and more specifically, about 5-10 milligrams daily, or about 8 milligrams daily. In this embodiment, blood serum levels preferably reach at least about 2 ng/ml, may reach about 10 to about 35 ng/ml, or most preferably about 20-30 ng/ml. (Sicotte et al., *Neurology*, 56:A75.) In some embodiments, estradiol (E2) levels would preferably reach at least about 2 ng/ml and most preferably about to 10-35 ng/ml. In some embodiments, estrone (E1) levels would preferably reach at least about 2 ng/ml and most preferably about 5-18 ng/ml (De-Groot and Jameson, 1994).

In one embodiment, the dosage may be selected to be between about 0.1 and 2.0 milligrams of α or β estradiol, or about 0.05 to 0.5 milligrams conjugated estrogen.

The dosage of the primary agent may be selected for an individual patient depending upon the route of administration, severity of disease, age and weight of the patient, other medications the patient is taking and other factors normally considered by the attending physician, when determining the individual regimen and dosage level as the most appropriate for a particular patient.

The use of this group of primary agents is advantageous in at least that other known or experimental treatments for cellular mediated autoimmune diseases are chemotherapeutic immunosuppresants which have significant risks and side effects to patients, including decreasing the ability of the patient to fight infections, inducing liver or heart toxicity which are not caused by estrogen treatment. Other agents used in MS do not cause these side effects, but are associated with flu-like symptoms or chest tightness. Further, these previously used agents are associated with local skin reactions since they entail injections at frequencies ranging from daily to once per week.

DOSAGE FORM. The therapeutically effective dose of the primary agent included in the dosage form is selected at least by considering the type of primary agent selected and the mode of administration. The dosage form may include the active primary agent in combination with other inert ingredients, including adjutants and pharmaceutically acceptable carriers for the facilitation of dosage to the patient as known to those skilled in the pharmaceutical arts. The dosage form may be any form suitable to cause the primary agent to enter into the tissues of the patient.

In one embodiment, the dosage form of the primary agent is an oral preparation (liquid, tablet, capsule, caplet or the like) which when consumed results in elevated serum estrogen levels. The oral preparation may comprise conventional carriers including dilutents, binders, time release agents, lubricants and disinigrants.

Possible oral administration forms are all the forms known from the prior art such as, tablets, dragees, pills or capsules, which are produced using conventional adjuvants and carrier substances. In the case of oral administration it has proved appropriate to place the daily units, which in case comprise a combination of the two agents, in a spatially separated and individually removable manner in a packaging unit, so that it is easy to check whether the typically daily taken, oral administration form has in fact been taken as it is important to ensure that there are no taking-free days. Depot injections can be administered at 1 to 6 months or longer intervals. Hormonal implants contain both hormonal components and deliver the same over a period of preferably 3 to 6 months.

In other embodiments of the invention, the dosage form may be provided in a topical preparation (lotion, creme, ointment, patch or the like) for transdermal application. Alternatively, the dosage form may be provided in a suppository or the like for intravaginal or transrectal application. Alternatively, the agents may be provided in a form for injection or for implantation.

In the transdermal administration of the combination according to the invention, the two hormonal agents may be applied to a plaster or also can be applied by transdermal, therapeutic systems and are consequently supplied to the organism. For example, an already prepared combination of the two hormonal components or the latter individually can be introduced into such a system, which is based on ionotherapy or diffusion or optionally a combination of these effects.

That estrogens or estrogen receptor active agents can be delivered via these dosage forms is advantageous in that currently available therapies, for MS for example, are all injectables which are inconvenient for the user and lead to decreased patient compliance with the treatment. Non-injectable dosage forms are further advantageous over current injectable treatments which often cause side effects in patients including flu-like symptoms (particularly, β interferon) and injection site reactions which may lead to lipotrophy (particularly, glatiramer acetate copolymer-1).

However, in additional embodiments, the dosage form may also allow for preparations to be applied subcutaneously, intravenously, intramuscularly or via the respiratory system.

SECONDARY ACTIVE AGENTS. Any one or a combination of secondary active agents may be included in the dosage form with the primary agent. Alternatively, any one or a combination of secondary active agents may be administered independently of the primary agent, but concurrent in time such that the patient is exposed to at least two agents for the treatment of their immunological disease.

The secondary agents are preferably immunotherapeutic agents, which act synergistically with the primary agent to diminish the symptomology of the autoimmune disease. Secondary active agents may be selected to enhance the effect of the estrogen or estrogen receptor active agent, reduce the effect of the estrogen or estrogen receptor active agent or effect a different system than that effected by the estrogen or estrogen receptor active agent.

Secondary active agents include immunotherapeutic agents which cause a change in the activity or function of the immune system.

In one embodiment, a secondary agent may be a therapeutically effective amount of one or more gestagens, for example, progesterone, chlormadinone acetate norethisterone acetate, norethindrone, cyproterone acetate, desogestrel, levonorgestrel, other natural and/or synthetic gestagens, antigestagens and hormonal compounds which split off at least one gestagen following taking. For example, the gestagen may be a progesterone, precursor, analog or progesterone receptor agonist or antagonist. In one embodiment, the secondary agent is 100-200 milligrams of progesterone administered daily. Progesterone in combination with estrogen or estrogen receptor active agent treatment is advantageous in at least protecting patients against risks associated with long term estrogen exposure, including, but not limited to endometrial proliferation and breast cancers.

Norethindrone may be selected as the secondary agent in premenapausal and perimenapausal women cycling (age 18-50 approximately) at doses of 0.35 mg per day continuously. If breakthrough bleeding occurs, then the dose may be increased to 0.70 mg per day temporarily (for 2-6 months). Then the lower dose of 0.35 mg per day may be resumed.

Norethindrone can also be given in noncycling, menopausal women (age over 50 approximately) at minimal doses of 0.70 mg per day for about 2-4 weeks duration, every 2-4 month, and more specifically every about 3 months. In this manner, when norethindrone is given for 2 weeks every 3 months.

By way of further example, the compositions may be formulated and treatment provided, such that the composition comprises about 1-20 mg estriol and about 0.2-3 mg norethindrone. Further, the composition may include norethindrone administered at doses of about 0.5 to 3.0 mg per day for a period of about 2-4 weeks, then the dose of norethindrone may reduced to a dose of about 0.2 to 0.5 mg thereafter.

By way of further example, the compositions may be formulated and treatment provided, such that the composition comprises about comprising about 1-20 mg estriol and about 50-100 mg progesterone. Further, progesterone may be administered at doses of about 50-100 mg per day for a period of about 2-4 weeks, then the dose of progesterone may be reduced to a dose of about 25-50 mg thereafter. A higher dose may given at a selected interval (such as every 2-4 weeks) for a selected period of time (such as every 2-4 months) to diminish endometrial proliferation.

The secondary agent is advantageous at least in preventing endometrial proliferation which may arise from prolonged use of estrogens, such as estriol.

In another embodiment, a third agent may be added to the combination at a therapeutically effective amount. Preferably the third agent may be administered at a lower dose due to the synergistic effect with the combination of the first and second agents. Examples include a glucocorticoid, precursor, analog or glucocorticoid receptor agonist or antagonist. For example, prednisone may be administered, most preferably in the dosage range of about 5-60 milligrams per day. Also, methyl prednisone (Solumedrol) may be administered, most preferably in the dosage range of about 1-2 milligrams per day. Glucocorticoids are currently used to treat relapse episodes in MS patients, and symptomatic RA within this dosage range.

In other embodiments, a third agent may be selected from the group immunotherapeutic compounds. For example, as O-interferon (Avonex® (interferon-beta 1a), Rebiff® (by Serono); Biogen, Betaseron® (interferon-beta 1b; Berlex, Schering), glatiramer acetate copolymer-1 (Copaxone®; Teva), antineoplastics (such as mitoxantrone; Novatrone® Lederle Labs), human monoclonal antibodies (such as natalizumab; Antegren® Elan Corp. and Biogen Inc.), immonusuppressants (such as mycophenolate mofetil; CellCept® Hoffman-LaRoche Inc.), paclitaxel (Taxol®; Bristol-Meyers Oncology), cyclosporine (such as cyclosporin A), corticosteroids (glucocorticoids, such as prednisone and methyl prednisone), azathioprine, cyclophosphamide, methotrexate, cladribine, 4-aminopyridine and tizanidine.

By way of example, which is consistent with the current therapeutic uses for these treatments, Avonex® in a dosage of about 0 to about 30 mcg may be injected intramuscularly once a week. Betaseron® in a dosage of about 0 to about 0.25 mg may be injected subcutaneously every other day. Copaxone® in a dosage of about 0 to about 20 mg may be injected subcutaneously every day. Finally, Rebiff® may be injected at a therapeutic dose and at an interval to be determined based on clinical trial data. However, dosages and method of administration may be altered to maximize the effect of these therapies in conjunction with estrogen treatment. Dosages may be altered using criteria that are known to those skilled in the art of diagnosing and treating autoimmune diseases.

Preferably, a third secondary agent would be administered in the dosage ranges currently used to treat patients having autoimmune diseases, including MS patients. Alternatively, the third agent may be administered at a reduced dose or with reduced frequency due to synergistic or duplicative physiological effects with the primary and secondary agents.

Preferably, patients exhibiting symptomology of autoimmune diseases are treated with the above agents. Most preferably, patients exhibit autoimmune diseases marked by improvement in delayed onset or symptomology at least during a treatment regimen, including but not limited to that reflecting patterns observed during the second or third trimester of pregnancy.

In one embodiment the invention may achieve a continuous, combined administration of a product comprising two hormonal components, namely a first pregnancy hormonal component comprising, an estrogen or pregnancy hormone, such as estriol, and a second hormonal component comprising at least one gestagen, so that a continuous uninterrupted steady state of hormones can be administered to female patients (premenopausal or postmenopausal) suffering from autoimmune diseases (such as multiple sclerosis) and thereby reduce the onset and severity (such as relapse rates) of such disease. The invention also contemplates various dosing regiments whereby one or more gestagens are administered at higher doses for shorter periods of time to reduce endometrial side effects associated with hormonal treatment.

Currently, estrogens are not understood to cover steroid molecules, which preferably evolve their action in that they in different ways exert a biological effect at different cell locations in different organs. Estrogens can act on at least: (1) the cellular membrane, (2) intracellular, cytoplasmic proteins and (3) specific nuclear receptors. It has recently become known that besides the standard estrogen receptor type 1 there is a second estrogen receptor type 2, whose organ distribution is different from that of the estrogen receptor type 1. Thus, estrogens also include the compounds known as designer hormones, which have the aforementioned characteristics.

Biogenous estrogens include those estrogens which are produced by the human body and consequently include endogenic estrogens. The biogenous estrogens used in specific embodiments of the invention may be endogenous those which are chemically synthesized. However, it is fundamentally also possible to use compounds isolated from an organism.

Thus, biogenous estrogens include steroid molecules, which evolve an estrogen-like action on the membrane, cytoplasmic proteins and nuclear receptors for hydrophobic ring substances and consequently trigger biological effects corresponding to a hydrophobic steroid ring structure able to initiate an estrogen-like action in cells, organs and the complete organism.

Biogenous estrogens also include conjugate, biogenous estrogens, such as estradiol valerate and estrone sulphate.

Antiestrogens include hydrophobic ring structure substances and other substances able to specifically and selectively counteract the above-described estrogen action on cells, organs or the overall organism.

Continuous administration of agents in accordance with this disclosure includes an administration uninterrupted over the use period, in which there are no hormonal component taking-free intervals. This means that there is no planned interruption of the administration of the agents by administering placebos in place of the agents. Thus, over the entire administration period, the hormonal components forming the combination or agents according to the invention are administered uninterrupted. In some embodiments, the dosages of agents also remains unchanged. However, in some embodiments, the dosage of estrogen (understood in the full breadth of the concept defined here), and gestagen (also understood in the full breadth of the term defined here), can be difference for older women compared with younger women. This can also take place in such a way that over the continuous administration period initially there is a start with a specific dosage and this is then adapted over a period of weeks, months and/or years to the changed biological needs of the women through the administration of a subsequent dosage, but which also comprises a combination of primary and secondary agents according to the present invention.

As a result of the continuous administration of the primary and secondary agents, the natural hormonal processes taking place in the female organism do not interrupt contraceptive security.

It has surprisingly also been found that on administering the combination according to the invention there is a reliable continuous suppression of the menstrual cycle and menstruation in the case of a very low dosage. Without wishing to be bound by this explanation, the combination of the hormonal components, and in particular the low estrogen dosage would appear to be suitable for eliminating the otherwise conventional side effects of estriol and to drop below the administrations of more than 15 mg of estriol otherwise considered typically necessary in prior art contraceptives.

As a result of the estrogen component, respectively by specific action of hydrophobic ring substances with an estrogen-like action, there can be a suppression of gonadotropins. This is desirable. The resulting suppression of the ovarian function is compensated by an adequate substitution of estrogen action. This prevents the development of osteoporosis, the favorable vascular effects of estrogens are maintained, and there is no unfavorable influence to the lipid metabolism. By interrupting the cycle-dependent instability in the hormone system, premenstrual syndrome can be favorably influenced. In addition, the physiological equilibrium of the coagulation system is not disturbed, because the unstable equilibrium in which the coagulation system occurs is not activated and deactivated by the up and down of hormone fluctuations. Thus, the combination according to the invention is particularly suitable for women aged more than 40, where the risk of circulatory disturbances is known to increase with increasing age. There is also a reduction in the thrombosis risk, which has of late acquired considerable significance in contraceptive therapy.

The low dosages of the two hormonal components, and in particular the estrogen component, is made possible by the additive action of the two hormonal components, without there being any limitation to the action of the combination according to the invention with respect to its contraceptive and ovulation-inhibition properties.

KITS. In another aspect of this invention kits are provided for use by the treating physician in the clinic or prescribed patient for self-administration of treatment. The kits of this invention include at least one primary agent and one secondary agent in the appropriate dosages and dosage form for the treatment of the patient's clinical symptoms.

In one embodiment of the kit, the primary agent is estriol in doses of about 1-20, or about 5-10, or about 8 milligrams and the secondary agent is a gestagen, such as progesterone in doses of about 100 to about 200 milligrams. In a second embodiment of this kit, the primary agent is estradiol in doses of about 0.1 to 2 milligrams and the secondary agent is a gestagen.

In a third embodiment of this invention, the kit may also include a third agent of β-interferon in doses of about 0.25 milligrams of Betaseron® or about 30 mcg of Avonex®. In a fourth alternate embodiment of the kit, the third agent may be glatiramer acetate copolymer in doses of about 20 milligrams of Copaxone®.

The kit also preferably contains instructions for use of the kit by the use by the treating physician or patients to treat their autoimmune disease. Such information would include at least the schedule for the administration of the primary and secondary agent doses and, if included, a third agent dose.

Although the present invention has been described in terms of the preferred embodiment above, numerous modifications and/or additions to the above-described preferred embodiments would be readily apparent to one skilled in the art.

EXAMPLE 1

Methods: Trial Design. A crossover design was used with monthly brain MRIs during the six month pretreatment period, the six month treatment period with oral estriol (8 milligrams/day) and the six month post treatment period, with clinical and laboratory evaluations as demonstrated (FIG. 1A).

Inclusion Criteria. Women with clinically definite MS, ages 18-50, with an EDSS 0-6.5 who had been off interferon beta and copolymer-1 for at least six months, and had no steroid treatment for at least three months were eligible. At least 5 $cm^3$ of lesion burden on a screening T2 weighted brain MRI was required. Subjects who were pregnant or nursing, on oral contraceptives or hormone replacement therapy, or who had a history of thrombosis, neoplasm or gynecologic disease, or who had been treated in the past with total lymphoid irradiation, monoclonal antibody, T cell vaccination, cladribine or bone marrow transplantation were excluded.

Patients. Twelve female patients with clinically definite MS were enrolled. Six had RR disease and six had SP disease. All six RR and four of six SP patients completed the entire 18 month study period. One SP patient was discontinued from the study because of prolonged treatment with steroids for tonic spasms by an outside neurologist and the other did not wish to go untreated in the post treatment period. Of the ten patients who completed the entire study, the mean age was 44 years (range 28 to 50 years) and the mean EDSS was 3.3 (range 1.0 to 6.5). The mean EDSS score for the SP patients was 5.0 while the mean EDSS for the RR patients was 2.2. The 18 month trial was extended in RR patients whereby treatment was re-instituted.

Medication. For the initial treatment phase, micronized, U.S.P. graded estriol powder (Medisca, Inc., Plattsburg, N.Y.) was put into capsules by UCLA Pharmaceutical Services. During the extension re-treatment phase in the RR patients, all but one received a capsule of estriol (8 milligrams/day) plus progesterone (100 milligrams/day), while the single RR patient who had a hysterectomy received only estriol (8 milligrams/day) (Women's International Pharmacy, Madison, Wis.).

Clinical and Safety Measures. Subjects were evaluated using the Kurtzke's Expanded Disability Status Scale (EDSS) by the same neurologist (RV) throughout the study. At each visit the study nurse (RK) administered the paced auditory serial addition test (PASAT) and the 9-hole peg test. Blood was drawn for SMA12, cholesterol panel, blood counts and hormone levels (estriol, estradiol, estrone, LH, FSH, cortisol, progesterone). Estriol levels in serum were determined by ELISA according to manufacturer's instructions (Oxford Biomedical, Oxford, Mich.).

Delayed Type Hypersensitivity Responses (DTH). DTH to tetanus (Tetanus Toxoid, Wyeth Laboratories, Marietta, Pa.) and candida (Candin, Allermed Laboratories, San Diego, Calif.) were tested at two timepoints, once in the pretreatment period at study month 3 and once at the end of the treatment period at study month 12 (FIG. 1a). A group of six untreated healthy control women were also tested twice, spanning the same time interval (9 months). 0.1 ml of each solution was injected intradermally on the anterior surface of the forearm. Induration at each injection site was read after 48 hours. Each site was measured twice, once vertically and once horizontally with the average recorded. The same nurse (RK) administered all injections and read all responses on all subjects at both time points.

Reverse Transcription and Polymerase Chain Reaction. Peripheral blood mononuclear cells (PBMCs) were isolated from heparinized venous blood and cryopreserved. PBMCs were thawed in parallel from a given patient during the two pre-treatment timepoints and the two treatment timepoints. Total RNA was isolated, DNA was removed and mRNA was reverse transcribed. Both IFN-γ and actin were amplified from the same cDNA, however, the cDNA was diluted 1:9 prior to amplification for actin. Amplification was done in 1 mM MilligramsCl$_2$ using IFN-γ and actin primer sequences (Life Technologies, Rockville, Md.). omplementary DNA was amplified for 35 cycles: 45" @95° C., 60" @54° C. and 45" @72° C. PCR products were separated on a 1.5% agarose gel containing ethidium bromide and densitometry performed.

MRIs. Scans were performed on a 1.5T General Electric scanner. The pulse sequences obtained were a T1-weighted scan with and without gadolinium (Omniscan 0.1 mmol/kg) and a PD/T2 weighted scan. Digitized image data was transferred to a SGI workstation (Silicon Graphics, Inc) for further processing. The number and volume of new and total gadolinium enhancing lesions was determined using a semiautomated threshold based technique (Display, Montreal Neurological Institute) by a single experienced operator (NS). The operator was blinded as to whether patients had RR or SP disease. To calculate T2 volumes, a custom semiautomated, threshold based, seed-growing algorithm was used to determine lesion volume after skull stripping, rf correction and spatial normalization. All scans were counted by the same technician who was blinded as to whether patients had RR or SP disease.

Statistical Analysis. One sample, paired, t-tests were used to ascertain significance of percent changes in DTH responses, IFN-γ levels and PASAT cognitive testing scores during treatment as compared to pretreatment. The nonparametric, Wilcoxon's signed rank test was used for statistical comparisons in enhancing lesion numbers and volumes on MRI between the six month baseline period and each treatment period, post treatment period and re-treatment period.

Results. Estriol levels and tolerability. Serum estriol levels during treatment and re-treatment approximated those observed in women who were six months pregnant, but were lower than those who were 8.5 months pregnant (FIG. 1b). Consistent with previous reports, estriol was well tolerated with only menstrual cycle abnormalities. There were no significant alterations in any laboratory measures including LH, FSH, cortisol, progesterone, estradiol and estrone.

Figure 2B:
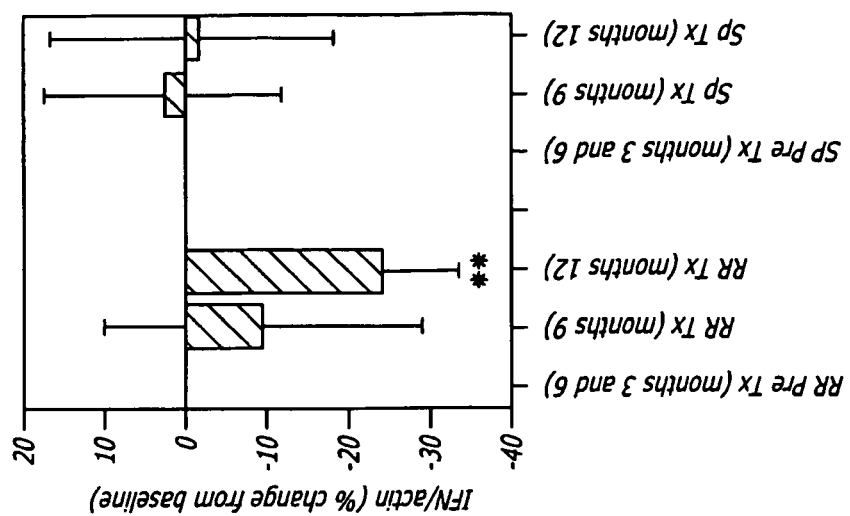
FIG. 2b is a bar graph depicting levels of IFN-γ between treatment groups.
Figure 2A:
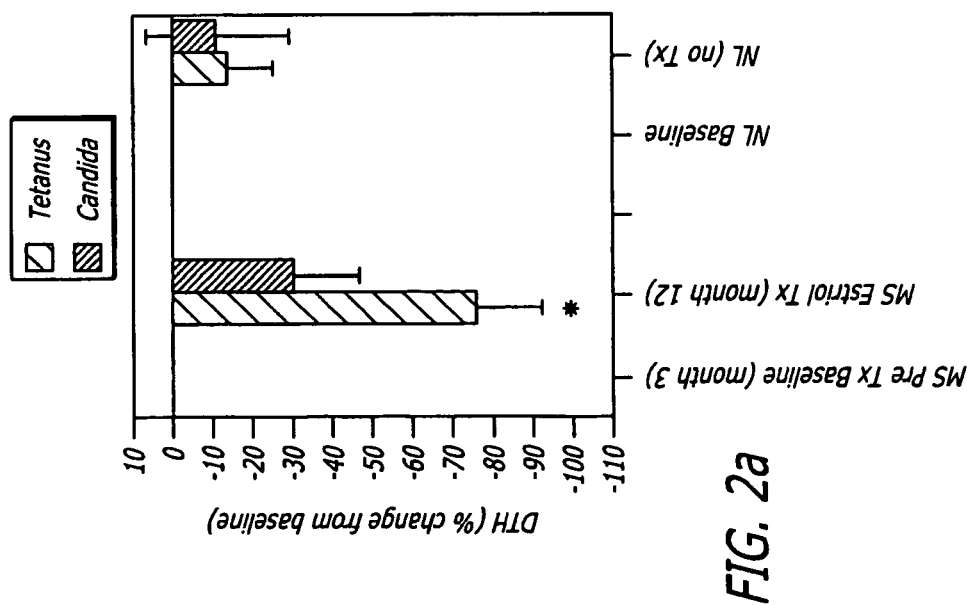
FIG. 2a is a bar graph describing the Delayed Type Hypersensitivity (DTH) responses to tetanus and to candida.

Immune Responses. Skin testing to tetanus and-candida were performed once in the pretreatment period and once at the end of the treatment period to determine whether they might be decreased with treatment. DTH responses to tetanus were significantly, P=0.006, decreased at study month 12, when patients had been on estriol for six months, as compared to DTH responses at study month 3, the pretreatment baseline (FIG. 2a). DTH responses to candida were decreased less dramatically and more variably. The significant decrease in DTH responses to tetanus from pretreatment (month 3) to treatment (month 12) was not merely due to repeat testing at nine months since healthy, untreated female controls tested at baseline, then again after nine months, did not demonstrate a significant decrease in DTH responses as compared to their baseline. These findings are consistent with an estriol induced down-regulation of Th1 responses in vivo during treatment.

IFN-γ is a signature cytokine for Th1 responses. Therefore, we assessed IFN-γ levels by RT-PCR of unstimulated peripheral blood mononuclear cells (PBMCs) derived ex vivo from patients during the pretreatment and the treatment periods. In the six RR patients, levels of IFN-γ were variably decreased at study month 9 (after three months of estriol treatment) and then significantly decreased, P=0.003, at study month 12 (after six months of estriol treatment) as compared to baseline pretreatment levels (months 3 and 6) (FIG. 2b). In contrast, there was no decrease in IFN-γ in the four SP patients. These data are consistent with the concept that the immune system of RR patients, as compared to SP patients, may be more amenable to treatments that aim to decrease Th1 responses. Also, the observation that estriol treatment can alter cytokine production by PMBCs is consistent with reports demonstrating estrogen receptors α and β in immune tissues and cells.

Figure 3A:
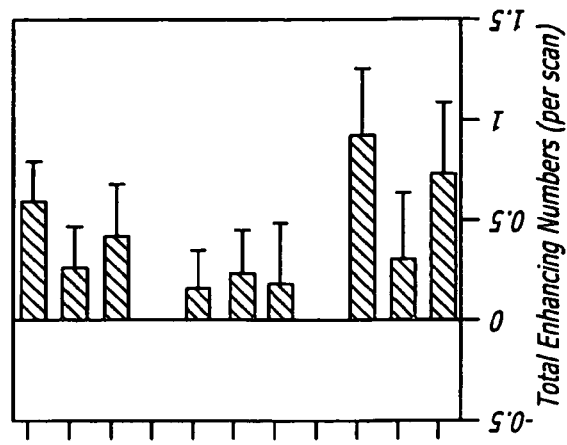
Figure 3B:
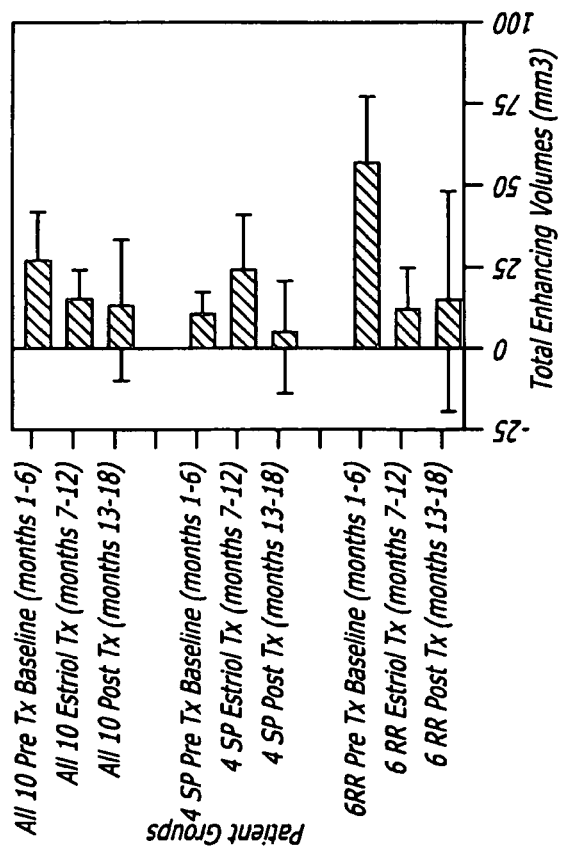
Figure 3D:
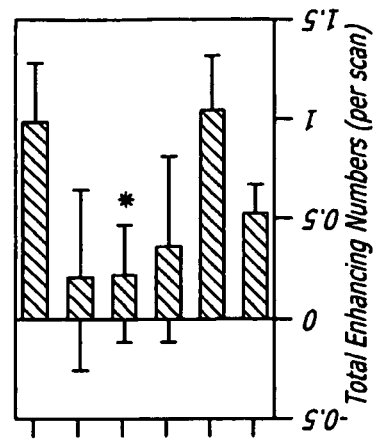
Figure 3C:
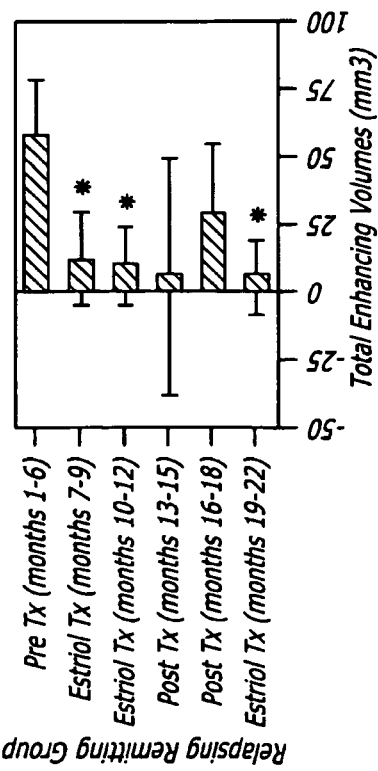

MRIs. Based on the protective effect of pregnancy on relapse rates in MS patients and the association of gadolinium enhancing lesions with relapses, we hypothesized that estriol treatment would have an anti-inflammatory effect as manifested by decreases in enhancing lesions on serial brain MRIs. Compared to the six month pretreatment baseline period, the total volume and number of enhancing lesions for all ten MS patients (6RR, 4SP) decreased during the treatment period. This improvement in the group as a whole was driven by the beneficial effect of estriol treatment in the RR, not the SP, group (FIGS. 3a and 3b). Therapeutic effects of estriol treatment in the RR group were therefore examined in further detail. Within the first three months of treatment of RR patients, median total enhancing lesion volumes were decreased by 79%, P=0.02, and numbers were decreased by 82%, P=0.09 (FIGS. 3c and 3d). They remained decreased during the next three months of treatment, with lesion volumes decreased by 82%, P=0.01, and numbers decreased by 82%, P=0.02. In the post treatment period, median total enhancing lesion volumes and numbers became variable in the first three months off treatment, before returning to near baseline levels in the last three months of the post treatment period. During the four month re-treatment extension phase, enhancing lesion volumes decreased again by 88%, P=0.008, and numbers decreased again, this time by 48%, P=0.04, as compared to original baseline (FIGS. 3c and 3d). Changes in median new enhancing lesion volumes and numbers followed similar patterns as median total lesion numbers and volumes (FIGS. 3e and 3f).

Median T2 lesion volumes for the whole group were 15.3 cm$^3$ (range 6.1-33.8), with no significant differences in median T2 volumes between RR and SP groups. Consistent with enhancing lesion data, serial T2 lesion volumes revealed that estriol treatment tended to be most beneficial in RR patients. In the RR group, median T2 lesion volumes remained stable during the six month treatment period (0% change), increased during the six month post treatment period (7.4% higher), and then declined in the four month re-treatment extension period (2.0% lower).

Clinical Measures. Relapses were few and showed no significant changes during the study. In the six RR patients, one relapse occurred during the pretreatment period, one in the treatment period, two in the post treatment period and none in the re-treatment period. No relapses occurred in SP patients. EDSS and 9 Hole Peg Test scores showed no significant changes during the study (Table 1).

TABLE 1

Clinical Measures

| | Pretreatment | | Estriol Treatment | | Post Treatment | |
|---|---|---|---|---|---|---|
| | 3 mo. | 6 mo. | 9 mo. | 12 mo. | 15 mo. | 18 mo. |
| EDSS scores | | | | | | |
| 6 RR | 2.2 (0.6) | 2.0 (0.5) | 1.5 (0.7) | 1.7 (0.6) | 1.8 (0.6) | 1.8 (0.5) |
| 4 SP | 5.0 (0.9) | 5.0 (0.9) | 4.9 (1.0) | 5.0 (0.9) | 5.1 (1.1) | 5.0 (0.8) |
| 9 Hole Peg Test scores | | | | | | |
| 6 RR | | | | | | |
| R | 22.2 (2.4) | 21.8 (1.6) | 22.5 (2.3) | 21.5 (1.9) | 21.0 (1.7) | 21.4 (2.4) |
| L | 24.8 (3.2) | 22.9 (1.6) | 24.3 (2.5) | 23.3 (2.1) | 23.0 (2.1) | 22.7 (2.3) |
| 4 SP | | | | | | |
| R | 26.8 (0.4) | 29.9 (2.4) | 30.2 (1.4) | 31.7 (4.8) | 29.4 (5.2) | 34.0 (8.7) |
| L | 23.5 (1.4) | 25.6 (2.5) | 22.7 (1.7) | 24.8 (2.6) | 26.7 (0.7) | 25.0 (1.8) |

Interestingly, PASAT cognitive testing scores were significantly improved in the RR-group, but not in the SP group (FIG. 4). This improvement in PASAT scores in RR patients by 14.0% during treatment as compared to baseline, reached statistical significance, P=0.04. It is unlikely that this improvement was entirely due to a practice effect of repeated testing because of the long time interval between testing (9 months) and because alternate versions of the test were used in each patient. This beneficial effect of estriol treatment on PASAT scores of RR MS patients is consistent with previous reports describing a beneficial effect of estrogen replacement therapy in surgically menopausal women and high dose estrogen treatment in Alzheimer's disease. (Sicotte, et al., Treatment of Women with Multiple Sclerosis Using Pregnancy Hormone Estradiol: A Pilot Study. *Neurology*, 56 (8 Supp. 3):A75, April 2001, and Sicottte, et al., Treatment of Multiple Sclerosis with the Pregnancy Hormone Estradiol, Submitted to *Neurology* 2002), herein incorporated by reference.

EXAMPLE 2

Progesterone in combination with estrogen treatments has been shown to protect against endometrial proliferation and cancer. Indeed, estrogen cannot be given for a lengthy period of time in an "unopposed" fashion in any woman with a uterus. Thus, seven of the 12 patients wanted to remain on estriol after completion of the 18 month study. These patients were then put back on 8 milligrams of estriol and 100 milligrams of progesterone per day. In an extension phase of the study which began after completion of the post treatment phase. This extension phase was 4 months in duration. Each of the seven patients had an MRI every month during the 4 month extension phase. Additionally, each of the seven patients was examined neurologically and had serologic studies done at the end of this phase. No known negative effects 100 milligrams of progesterone in combination therapy with 8 milligrams of estriol treatment were noted.

EXAMPLE 3

Method. A 33 year old white female relapsing remitting MS patient was treated with estriol 8 mg/day and norethindrone 0.35 mg/day, in combination with Copazone injections, to try to prevent post partum relapses which are known to occur at months 3-6 post partum.

History. Previously, when the patient had her first child (now age 7), she was treated with Copaxone (standard of MS care) and norethindrone (the progesterone only birth control pill) and relapsed at 6 weeks. When the patient had her second child (now age 3), she was again treated with Copaxone and norethindrone and again relapsed, this time at 4.5 months.

Results. When the patient had her third child (now 6 months of age), she resumed treatment with Copaxone as before. However on day 10 post partum she began taking estriol 8 mg orally each day in combination with norethindrone 0.35 mg/day. She had no relapses in the entire 6 month post partum period, and her neurologic exam remained unchanged with minimal disability (EDSS=1). Since monthly brain MRIs with gadolinium to detect enhancing MS lesions are more sensitive for inflammatory disease activity than clinical relapses, the patient underwent serial monthly MRIs at post partum months 4, 5, and 6. There was no enhancement at month 4, only one small enhancing lesion at month 5, and at 6 months only a small residual, less robust enhancement of the single lesion from the previous month. No new enhancement was observed at month 6. The T2 lesion load remained stable throughout.

She has had increased irregular menstrual bleeding despite using the progesterone minipill, one pill per day since day 10, to stabilize the uterine endometrium and for birth control. Uterine ultrasounds at month 3 and 6 showed a thin, not thick, endometrium, consistent with an unstable lining, not suggestive of hyperplasia. The patient doubled the progesterone minipill for 2 weeks (0.70 mg/day) to stabilize the endometrium. Otherwise no adverse events have been reported.

In closing, it is noted that specific illustrative embodiments of the invention have been disclosed hereinabove. However, it is to be understood that the invention is not limited to these specific embodiments.

Accordingly, the invention is not limited to the precise embodiments described in detail hereinabove. With respect to the claims, it is applicant's intention that the claims not be interpreted in accordance with the sixth paragraph of 35 U.S.C. §112 unless the term "means" is used followed by a functional statement.

While the specification describes particular embodiments of the present invention, those of ordinary skill can devise variations of the present invention without departing from the inventive concept.

What is claimed is:

1. A method for treating at least one sign or symptom of an autoimmune disease, comprising administering to a subject, for a continuous administration period, a gestagen and estriol, wherein said gestagen and estriol are administered at unchanged dosages throughout the administration period, and wherein said estriol is administered at a dosage of about 1-20 milligrams per day.

2. The method of claim 1, wherein the estriol administered at a dosage of about 5-10 milligrams per day.

3. The method of claim 1, wherein the estriol administered at a dosage of about 8 milligrams per day.

4. The method of claim 1, wherein the gestagen is selected from the group comprising progesterone, chlormadinone acetate, northisterone acetate, norethindrone, and cyproterone acetate.

5. The method of claim 1, wherein the autoimmune disease is selected from the group comprising: multiple sclerosis, psoriasis, myesthania gravis, rheumatoid arthritis, uveitis, myesthenia gravis, Sjogren's syndrome, Hashimoto's thyroiditis or lupus.

6. The method of claim 1, in which the patient is a premenopausal, perimenopausal or postmenopausal female.

7. A method of claim 1, further comprising administering a third agent selected from the group comprising: glatiramer acetate, interferon-β 1a, interferon-β 1b and sphingosine-1-phosphate receptor modulator.

8. The method of claim 1, wherein the administration is oral.

9. The method of claim 1, wherein the administration period is 12 months.

10. A method for prevention of relapse of an autoimmune disease, comprising administering to a subject, for a continuous administration period, a gestagen and estriol, wherein said gestagen and estriol are administered at unchanged dosages throughout the administration period, and wherein said estriol is administered at a dosage of about 1-20 milligrams per day.

11. The method of claim 10, wherein the estriol administered at a dosage of about 5-10 milligrams per day.

12. The method of claim 10, wherein the administered at a dosage of about 8 milligrams per day.

13. The method of claim 10, wherein the gestagen is selected from the group comprising progesterone, chlormadinone acetate, northisterone acetate, norethindrone, and cyprotherone acetate.

14. The method of claim 10, wherein the autoimmune disease is selected from the group comprising, multiple sclerosis, psoriasis, myesthania gravis, rheumatoid arthritis, uveitis, myesthenia gravis, Sjogren's syndrome, Hashimoto's thyroiditis or lupus.

15. The method of claim 10, in which the patient is a premenopausal, perimenopausal or postmenopausal female.

16. A method of claim 10, further comprising administering a third agent selected from the group comprising glatiramer acetate, interferon-β 1a, interferon-β 1b and sphingosine-1-phosphate receptor modulator.

17. The method of claim 10, wherein the administration is oral.

18. The method of claim 10, wherein the administration period is 12 months.

* * * * *